(12) United States Patent
Buchmann et al.

(10) Patent No.: US 8,841,311 B2
(45) Date of Patent: Sep. 23, 2014

(54) SULPHONE-SUBSTITUTED QUINAZOLINE DERIVATIVES AS IMMUNO-MODULATORS, THEIR PREPARATION AND USE AS MEDICAMENTS

(75) Inventors: Bernd Buchmann, Hohen Neuendorf (DE); Dirk Kosemund, Berlin (DE); Duy Nguyen, Berlin (DE); Arne Von Bonin, Glienicke-Nordbahn (DE)

(73) Assignee: Bayer Intellectual Property GmbH, Monheim (DE)

( * ) Notice: Subject to any disclaimer, the term of this patent is extended or adjusted under 35 U.S.C. 154(b) by 398 days.

(21) Appl. No.: 13/054,582

(22) PCT Filed: Jul. 18, 2009

(86) PCT No.: PCT/EP2009/005232
§ 371 (c)(1),
(2), (4) Date: Jan. 18, 2011

(87) PCT Pub. No.: WO2010/009845
PCT Pub. Date: Jan. 28, 2010

(65) Prior Publication Data
US 2011/0166168 A1 Jul. 7, 2011

(30) Foreign Application Priority Data
Jul. 24, 2008 (EP) .................................. 08075664

(51) Int. Cl.
*A61K 31/517* (2006.01)
*C07D 239/70* (2006.01)
*C07D 239/94* (2006.01)

(52) U.S. Cl.
CPC ..................... *C07D 239/94* (2013.01)

USPC ...................................... 514/266.23; 544/253

(58) Field of Classification Search
USPC ...................................... 514/266.23; 544/253
See application file for complete search history.

(56) References Cited

FOREIGN PATENT DOCUMENTS

| WO | 0047212 A1 | 8/2000 |
| WO | 0121596 A1 | 3/2001 |
| WO | 2005007672 A2 | 1/2005 |

OTHER PUBLICATIONS

World IP Organization. "International Search Report." PCT/EP2009/005232, Applicant: Bayer Schering Pharma AG, Mailed: Sep. 25, 2009.

*Primary Examiner* — James O Wilson
*Assistant Examiner* — Oluwafemi Masha

(57) ABSTRACT

The present invention relates to sulphone-substituted quinazoline derivatives of the formula (I), processes for their preparation and their use as a medicament for the treatment of various diseases.

7 Claims, No Drawings

SULPHONE-SUBSTITUTED QUINAZOLINE DERIVATIVES AS IMMUNO-MODULATORS, THEIR PREPARATION AND USE AS MEDICAMENTS

The present invention relates to sulphone-substituted quinazoline derivatives, processes for their preparation, and their use as a medicament for the treatment of various diseases.

BIOLOGICAL BACKGROUND

An over-reacting immune system is co-responsible for numerous chronic inflammatory diseases, such as, for example, rheumatoid arthritis, Crohn's disease, asthma and multiple sclerosis. Owing to an increased release of proinflammatory cytokines, damage to endogenous tissue structures results. The interplay of the innate and adaptive immune system is of central importance in this context (Akira et al., 2001). Modulation of the immune system by substances which interfere with the activation of cells of the innate and/or of the adaptive immune system has an anti-inflammatory action and can thus attenuate the pathological phenotype in the diseases mentioned by way of example above.

Innate immunity is based on the fact that microorganisms such as bacteria and viruses have certain inherent features by means of which they are recognized by the immune system and subsequently activate. Certain pathogen-associated molecular patterns (PAMPs) are recognized. PAMPs are recognized by the pattern recognition receptors (PRR), which also include toll-like receptors (TLR) (Janeway and Medzhitov, 2002). TLRs are homologues of the Drosophila receptor protein toll. Humans have ten different TLRs. TLR one and six are co-receptors for TLR2. TLR2 recognizes, inter alia, lipoproteins and lipopeptides. TLR3 recognizes double-stranded RNA. TLR4 recognizes, inter alia, LPS of gram-negative bacteria and lipoteichoic acid of gram-positive bacteria. TLR5 recognizes flagellin. TLR9 recognizes CpG motifs in bacterial DANN (O'Neill, 2006). Co-receptors can further modify the recognition capabilities of TLRs (Jiang et al., 2005).

IL-1/-18, TLR Signal Transduction

TLRs are related to IL-1/IL-18 cytokine receptors in signal transmission. IL-1 ("endogenous pyrogen") strongly stimulates inflammation and induces fever. Members of the IL-1R/TLR superfamily have a TIR domain (toll/IL1 receptor). The TIR domain is approximately 200 amino acids long and contains three conserved sequence motifs. Proteins bearing TIR domains bind by means of a protein-protein interaction (O'Neill et al., 2005). The subclass one (1L-1R family) contains three Ig-like domains; the receptor is a heterodimer. These include the IL-1 receptors one and two, the co-receptor IL-1 RAcP and the corresponding proteins of the 1L-18 system. The subclass two (TLR family) contains leucine-rich motifs. Toll-like receptors form homo- or heterodimers.

After activation of the TLR or IL-1, -18 receptors by the appropriate ligands, a multistage signal cascade is set in motion. The TLR or IL-1/-18 receptor complex interacts with the adaptor protein MyD88 by means of TIR/TIR contacts. The IL-1 associated receptor kinase (IRAK-1) normally has Tollip (toll interacting protein) bound, which probably acts as an alleviating molecule ("silencer"). IRAK/Tollip binds to the active TLR/IL-1R complex. MyD88 displaces Tollip whereby IRAK1 and IRAK-4 are activated, very highly probably as a dimer by transphosphorylation. Active IRAK leaves the receptor and binds in the cytoplasm to the adapter molecule TRAF (Barton and Medzhitov, 2003). By means of TRAF, further proteins are ubiquitinylated. By means of an unknown mechanism, Ub-TRAF leads to the autophosphorylation of the S/T kinase TAK1 (a MAP kinase kinasekinase). TAK1 phosphorylates IκB (NF-κB activation) and MKK6. The latter is responsible for the activation of the MAP kinases p38 and JNK. NF-κB has been identified as a nuclear factor for the expression of the light antibody chain kappa in B cells, but is also involved in the regulation of many other genes. NF-κB is retained in the cytoplasm in the inactive state, where it is bound to the inhibitor IκB (Deng et al., 2000). Phosphorylation of IκB causes the inhibitor IkB to be proteolytically degraded and the transcription factor can migrate into the core. NF-κB is a heterodimer of the subunits p65 (Rel) and p50 (Bäuerle and Henkel, 1994). There are a number of members of this family which can interact in different ways. NF-κB on its own cannot induce transcription. For gene activation, transcriptional co-activators are necessary, such as, for example, p300 or CBT (Akira and Takeda, 2004).

The structures of the following patent applications form the structurally obvious prior art:

Benzyloxy-substituted quinazoline derivatives are mentioned in the following patent applications:. WO 2006/076246 (Inhibitors of serine proteases), but an amide side chain at the benzyl position is absolutely imperative. WO 93/17682 (angiotensine-II-receptor antagonists). Sulphonyl is not disclosed as a substituent.

Starting from this prior art, the object of the present invention consists in preparing further structures for therapy, in particular for immunomodulation.

The object is achieved by sulphone-substituted compounds of the general formula (I),

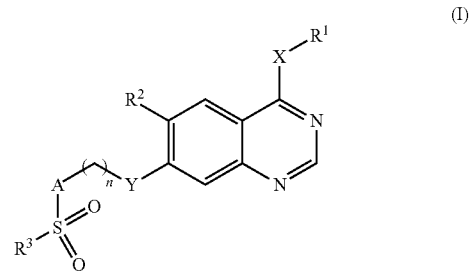

in which
$R^1$ represents
(i) a mono- or polysubstituted aryl or heteroaryl ring optionally identically or differently substituted by hydroxyl, —NR$^6$R$^7$, —NR$^5$—C(O)—R$^{10}$, —NR$^5$—C(O)—OR$^{10}$, —NR$^5$—C(O)—NR$^6$R$^7$, —NR$^6$—SO$_2$—R$^{10}$, cyano, halogen, $C_1$-$C_6$-alkoxy, —OCF$_3$, —CF$_3$, $C_3$-$C_6$-cycloalkyl and/or heterocyclyl having 3 to 8 ring atoms, or
(ii) a $C_1$-$C_6$-alkyl, $C_2$-$C_6$-alkenyl or $C_2$-$C_6$-alkynyl radical optionally identically or differently mono- or polysubstituted by hydroxyl, —NR$^6$R$^7$, —NR$^5$—C(O)R$^{10}$, —NR$^5$—C(O)—OR$^{10}$, —NR$^5$—C(O)—NR$^6$R$^7$, —NR$^5$—SO$_2$—R$^{10}$, cyano, halogen, $C_1$-$C_6$-alkoxy, —OCF$_3$, —CF$_3$, $C_3$-$C_6$-cycloalkyl and/or heterocyclyl having 3 to 8 ring atoms, or
(iii) a $C_3$-$C_6$ cycloalkyl or heterocyclyl ring having 3 to 8 ring atoms and optionally identically or differently mono- or polysubstituted by hydroxyl, —NR$^6$R$^7$, —NR$^5$—C(O)—R$^{10}$, —NR$^5$—C(O)—OR$^{10}$, —NR$^5$—C(O)—NR$^6$R$^7$, —NR$^5$—SO$_2$—R$^{10}$, cyano, halogen, $C_1$-$C_6$-alkoxy, —$OCF_3$, —$CF_3$, $C_1$-$C_6$-alkyl, $C_3$-$C_6$-cycloalkyl and/or heterocyclyl having 3 to 8 ring atoms, $R^2$ represents
- (i) hydrogen,
- (ii) hydroxyl, halogen, cyano, nitro, —$CF_3$, —$OCF_3$, —$C(O)OR^{10}$—$C(O)OH$, —$C(O)NR^6R^7$, —$C(S)NR^6R^7$, —$NR^6R^7$, —$NR^5$—$C(O)$—$R^{10}$, —$NR^5$—$C(O)$—$OR^{10}$, —$NR^5$—$C(O)$—$NR^6R^7$, —$NR^5$—$SO_2$—$R^{10}$, or
- (iii) a $C_1$-$C_6$-alkyl or $C_1$-$C_6$-alkoxy radical optionally identically or differently mono- or polysubstituted by halogen, hydroxyl, $C_1$-$C_6$-alkoxy, —$CF_3$, —$OCF_3$ or —$NR^6R^7$, or
- (iv) a $C_3$-$C_8$-cycloalkyl ring optionally identically or differently mono- or polysubstituted by halogen, hydroxyl, $C_1$-$C_6$-alkoxy, —$CF_3$, —$OCF_3$, —$NR^6R^7$ and/or $C_1$-$C_6$-alkyl, $R^3$ represents
a $C_1$-$C_6$-alkyl, $C_2$-$C_6$-alkenyl or $C_2$-$C_6$-alkynyl radical, a $C_3$-$C_7$-cycloalkyl or aryl ring, a heterocyclyl ring having 3 to 8 ring atoms or a monocyclic heteroaryl ring, in each case itself optionally identically or differently mono- or polysubstituted by hydroxyl, —$C(O)OR^{10}$, —$C(O)NR^6R^7$, —$NR^6R^7$, cyano, halogen, —$CF_3$, $C_1$-$C_6$-alkoxy, —$OCF_3$ and/or $C_1$-$C_6$-alkyl, X, Y independently of one another represents —O— or the group —$NR^4$—, A an aryl or heteroaryl ring optionally identically or differently mono- or polysubstituted by hydroxyl, —$NR^6R^7$, —$NR^5$—$C(O)$—$R^{10}$, —$C(O)NR^6R^7$, —$NR^5$—$C(O)$—$OR^{10}$, —$NR^5$—$C(O)$—$NR^6R^7$, —$NR^5SO_2$—$R^{10}$, cyano, halogen, $C_1$-$C_6$-alkoxy, —$OCF_3$, —$CF_3$, $C_1$-$C_6$-alkyl, $C_3$-$C_6$-cycloalkyl and/or heterocyclyl having 3 to 8 ring atoms, n represents 1-6, $R^4$ represents
- (i) hydrogen,
- (ii) a $C_1$-$C_6$-alkyl radical, $C_3$-$C_8$-cycloalkyl or aryl ring, a heterocyclyl ring having 3 to 8 ring atoms or a heteroaryl ring, or
- (iii) —$C(O)$—($C_1$-$C_6$)-alkyl, —$C(O)$-phenyl, or —$C(O)$-benzyl, (ii) and (iii) optionally being identically or differently mono- or polysubstituted by hydroxyl, —$NR^8R^9$, cyano, halogen, —$CF_3$, $C_1$-$C_6$-alkoxy and/or —$OCF_3$, or, if X represents —$NR^4$—, alternatively X, $R^1$ and $R^4$ together form a 3- to 8-membered ring which optionally, in addition to the nitrogen atom, contains one or more further heteroatoms, is optionally identically or differently mono- or polysubstituted by hydroxyl, $C_1$-$C_6$-alkyl, $C_1$-$C_6$-alkoxy, —$C(O)R^{10}$, —$SO_2R^{10}$, halogen or the group —$NR^8R^9$, optionally contains 1 to 3 double bonds and/or is optionally interrupted by one or more —$C(O)$— groups, $R^5$ represents hydrogen or a $C_1$-$C_6$-alkyl radical, $R^6$ and $R^7$ independently of one another represent
- (i) hydrogen and/or
- (ii) a $C_1$-$C_6$-alkyl radical, $C_2$-$C_6$-alkenyl, $C_3$-$C_8$-cycloalkyl and/or aryl ring, a heterocyclyl ring having 3 to 8 ring atoms and/or a heteroaryl ring,
  are optionally identically or differently mono- or polysubstituted by hydroxyl, —$NR^8R^9$, cyano, halogen, —$CF_3$, $C_1$-$C_6$-alkoxy and/or —$OCF_3$, or $R^6$ and $R^7$ together with the nitrogen atom form a 5- to 7-membered ring, which optionally, in addition to the nitrogen atom, contains 1 or 2 further heteroatoms and which can be identically or differently mono- or polysubstituted by hydroxyl, —$NR^8R^9$, cyano, halogen, —$CF_3$, $C_1$-$C_6$-alkyl, 1-$C_6$-alkoxy and/or —$OCF_3$, $R^8$ and $R^9$ independently of one another represent hydrogen or a $C_1$-$C_6$-alkyl radical which is optionally identically or differently mono- or polysubstituted by hydroxyl or halogen, $R^{10}$ represents a $C_1$-$C_6$-alkyl, $C_2$-$C_6$-alkenyl or $C_2$-$C_6$-alkynyl radical, a $C_3$-$C_8$-cycloalkyl or aryl ring, a heterocyclyl ring having 3 to 8 ring atoms or a heteroaryl ring,
  in each case optionally itself identically or differently mono- or polysubstituted by hydroxyl, halogen, cyano, nitro, —$NR^6R^7$, $C_1$-$C_6$-alkyl, —$CF_3$, $C_1$-$C_6$-alkoxy and/or —$OCF_3$, and their salts, diastereomers and enantiomers.

The following definitions underlie the invention:

$C_n$-Alkyl:

Monovalent, straight-chain or branched, saturated hydrocarbon radical having n carbon atoms.

A $C_1$-$C_6$ alkyl radical comprises, inter alia, for example:
methyl-, ethyl-, propyl-, butyl-, pentyl-, hexyl-, iso-propyl-, iso-butyl-, sec-butyl, tert-butyl-, iso-pentyl-, 2-methylbutyl-, 1-methylbutyl-, 1-ethylpropyl-, 1,2-dimethylpropyl, neo-pentyl-, 1,1-dimethylpropyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-, 1,2-dimethylbutyl-.

A methyl, ethyl, propyl or isopropyl radical is preferred.

$C_n$-Alkenyl:

Monovalent, straight-chain or branched hydrocarbon radical having n carbon atoms and at least one double bond.

A $C_2$-$C_6$ alkenyl radical comprises, inter alia, for example:
vinyl-, (E)-2-methylvinyl-, (Z)-2-methylvinyl-, homoallyl-, (E)-but-2-enyl-, (Z)-but-2-enyl-, (E)-but-1-enyl-, (Z)-but-1-enyl-, pent-4-enyl-, (E)-pent-3-enyl-, (Z)-pent-3-enyl-, (E)-pent-2-enyl-, (Z)-pent-2-enyl-, (E)-pent-1-enyl-, (Z)-pent-1-enyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, (E)-hex-1-enyl-, (Z)-hex-1-enyl-, isopropenyl-, 2-methylprop-2-enyl-, 1-methylprop-2-enyl-, 2-methylprop-1-enyl-, (E)-1-methylprop-1-enyl-, (Z)-1-methylprop-1-enyl-, 3-methylbut-3-enyl-, 2-methylbut-3-enyl-, 1-methylbut-3-enyl-, 3-methylbut-2-enyl-(E)-2-methylbut-2-enyl-, (Z)-2-methylbut-2-enyl-, (E)-1-methylbut-2-enyl-, (Z)-1-methylbut-2-enyl-, (E)-3-methylbut-1-enyl-, (Z)-3-methylbut-1-enyl-, (E)-2-methylbut-1-enyl-, (Z)-2-methylbut-1-enyl-, (E)-1-methylbut-1-enyl-, (Z)-1-methylbut-1-enyl-, 1,1-dimethylprop-2-enyl-, 1-ethylprop-1-enyl-, 1-propylvinyl-, 1-isopropylvinyl-, 4-methylpent-4-enyl-, 3-methylpent-4-enyl-, 2-methylpent-4-enyl-, 1-methylpent-4-enyl-, 4-methylpent-3-enyl-, (E)-3-methylpent-3-enyl-, (Z)-3-methylpent-3-enyl-, (E)-2-methylpent-3-enyl-, (Z)-2-methylpent-3-enyl-, (E)-1-methylpent-3-enyl-, (Z)-1-methylpent-3-enyl-, (E)-4-methylpent-2-enyl-, (Z)-4-methylpent-2-enyl-, (E)-3-methylpent-2-enyl-, (Z)-3-methylpent-2-enyl-, (E)-2-methylpent-2-enyl-, (Z)-2-methylpent-2-enyl-, (E)-1-methylpent-2-enyl-, (Z)-1-methylpent-2-enyl-, (E)-4-methylpent-1-enyl-, (Z)-4-methylpent-1-enyl-, (E)-3-methylpent-1-enyl-, (Z)-3-methylpent-1-enyl-, (E)-2-methylpent-1-enyl-, (Z)-2-methylpent-1-enyl-, (E)-1-methylpent-1-enyl-, (Z)-1-methylpent-1-enyl-, 3-ethylbut-3-enyl-, 2-ethylbut-3-enyl-, 1-ethylbut-3-enyl-, (E)-3-ethylbut-2-enyl-, (Z)-3-ethylbut-2-enyl-, (E)-2-ethylbut-2-enyl-, (Z)-2-ethylbut-2-enyl-, (E)-1-ethylbut-2-enyl-, (Z)-1-ethyl-but-2-enyl-, (E)-3-ethylbut-1-enyl-, (Z)-3-ethylbut-1-enyl-, 2-ethylbut-1-enyl-, (E)-1-ethylbut-1-enyl-, (Z)-1-ethylbut-1-enyl-, 2-propylprop-2-enyl-, 1-propylprop-2-enyl-, 2-isopropylprop-2-enyl-, 1-isopropylprop-2-enyl-,(E)-2-propylprop-1-enyl-, (Z)-2-propylprop-1-enyl-, (E)-1-propylprop-1-enyl-, (Z)-1-propylprop-1-enyl-, (E)-2-isopropylprop-1-enyl-, (Z)-2-isopropylprop-1-enyl-, (E)-1-isopropylprop-1-enyl-, (Z)-1-isopropylprop-1-enyl-, (E)-3,3-dimethylprop-1-enyl-, (Z)-3,3-dimethylprop-1-enyl-, 1-(1,1-dimethylethyl)ethenyl.

A vinyl or allyl radical is preferred.

$C_n$-Alkynyl:

Monovalent, straight-chain or branched hydrocarbon radical having n carbon atoms and at least one triple bond.

A $C_2$-$C_6$ alkynyl radical comprises, inter alia, for example:
ethynyl-, prop-1-ynyl-, prop-2-ynyl-, but-1-ynyl-, but-2-ynyl-, but-3-ynyl-, pent-1-ynyl-, pent-2-ynyl-, pent-3-ynyl-, pent-4-ynyl-, hex-1-ynyl-, hex-2-ynyl-, hex-3-ynyl-, hex-4-ynyl-, hex-5-ynyl-, 1-methylprop-2-ynyl-, 2-methylbut-3-ynyl-, 1-methylbut-3-ynyl-, 1-methylbut-2-ynyl-, 3-methylbut-1-ynyl-, 1-ethylprop-2-ynyl-3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl-, 1-ethylbut-3-ynyl-, 1-ethylbut-2-ynyl-, 1-propylprop-2-ynyl-, 1-isopropylprop-2-ynyl-, 2,2-dimethylbut-3-ynyl-, 1,1-dimethylbut-3-ynyl-, 1,1-di-methylbut-2-ynyl- or a 3,3-dimethylbut-1-ynyl-.

An ethynyl-, prop-1-ynyl- or prop-2-ynyl- radical is preferred.

$C_n$-Cycloalkyl:

Monovalent, cyclic hydrocarbon ring having n carbon atoms.

$C_3$-$C_7$-Cycloalkyl ring comprises:
cyclopropyl, cyclobutyl, cyclopentyl, cyclohexyl and cycloheptyl.

A cyclopropyl, cyclobutyl, cyclopentyl or a cyclohexyl ring is preferred.

$C_n$-Alkoxy:

Straight-chain or branched $C_n$-alkyl ether radical of the formula —OR with R=alkyl.

Aryl

Aryl is a monovalent, aromatic ring system without a heteroatom.

$C_6$-aryl is equal to phenyl. $C_{10}$-aryl ist equal to naphthyl.

Unless stated otherwise, aryl comprises only phenyl and napthyl.

Phenyl is preferred.

Heteroatoms

Heteroatoms are to be understood as meaning oxygen, nitrogen or sulphur atoms.

Heteroaryl

Heteroaryl is a monovalent, aromatic ring system having at least one heteroatom different from a carbon. Heteroatoms which can occur are nitrogen atoms, oxygen atoms and/or sulphur atoms. The bond valency can be on any desired aromatic carbon atom or on a nitrogen atom.

Unless stated otherwise, heteroaryl comprises only monocyclic and bicyclic

A monocyclic heteroaryl ring according o the present invention has 5 or 6 ring atoms.

Heteroaryl rings having 5 ring atoms comprise, for example, the rings:
thienyl, thiazolyl, furanyl, pyrrolyl, oxazolyl, imidazolyl, pyrazolyl, isoxazolyl, isothiazolyl, oxadiazolyl, triazolyl, tetrazolyl and thiadiazolyl.

Heteroaryl rings having 6 ring atoms comprise, for example, the rings:
pyridyl, pyridazinyl, pyrimidinyl, pyrazinyl and triazinyl.

A bicyclic heteroaryl ring according to the present invention has 9 or 10 ring atoms.

Heteroaryl rings having 9 ring atoms comprise, for example, the rings:
phthalidyl, thiophthalidyl, indolyl, isoindolyl, indazolyl, benzothiazolyl, indolonyl, isoindolonyl, benzofuranyl, benzothienyl, benzimidazolyl, benzoxazolyl, azocinyl, indolizinyl, purinyl.

Heteroaryl rings having 10 ring atoms comprise, for example, the rings:
isoquinolinyl-, quinolinyl-, benzoxazinonyl-, phthalazinonyl, quinolonyl-, isoquinolon-yl-, quinazolinyl-, quinoxalinyl-, cinnolinyl-, phthalazinyl-, 1,7- or 1,8-naphthyridinyl-, quinolinyl-, isoquinolinyl-, quinazolinyl- or quinoxalinyl-.

Monocyclic heteroaryl rings having 5 or 6 ring atoms are preferred.

Heterocyclyl

Heterocyclyl within the meaning of the invention is a completely hydrogenated heteroaryl (completely hydrogenated heteroaryl =saturated heterocyclyl), i.e. a non-aromatic ring system having at least one heteroatom different from a carbon. Heteroatoms which can occur are nitrogen atoms, oxygen atoms and/or sulphur atoms. The bond valency can be on any desired carbon atom or on a nitrogen atom.

Heterocyclyl ring having 3 ring atoms comprises, for example:
aziridinyl.

Heterocyclyl ring having 4 ring atoms comprises, for example:
azetidinyl, oxetanyl.

Heterocyclyl rings having 5 ring atoms comprise, for example, the rings: pyrrolidinyl, imidazolidinyl pyrazolidinyl and tetrahydrofuranyl.

Heterocyclyl rings having 6 ring atoms comprise, for example, the rings: piperidinyl, piperazinyl, morpholinyl, tetrahydropyranyl and thiomorpholinyl Heterocyclyl ring having 7 ring atoms comprises, for example: azepanyl, oxepanyl, [1,3]-diazepanyl, [1,4]-diazepanyl.

Heterocyclyl ring having 8 ring atoms comprises, for example: oxocanyl, azocanyl Unless stated otherwise, heterocyclyl denotes a heterocyclyl ring having 3 to 8 ring atoms.

Halogen

The designation halogen comprises fluorine, chlorine, bromine and iodine.

Compounds of the general formula (I) form a preferred subgroup, in which $R^1$ represents (i) a heteroaryl ring optionally identically or differently mono- or polysubstituted by hydroxyl, —$NR^6R^7$, cyano, halogen, $C_1$-$C_6$-alkoxy, —$NR^5$—$C(O)R^{10}$, —$OCF_3$, —$CF_3$, $C_1$-$C_6$-alkyl, or (ii) a $C_1$-$C_6$-alkyl radical optionally identically or differently mono- or polysubstituted by hydroxyl, —$NR^6R^7$, cyano, halogen, $C_1$-$C_6$-alkoxy, —$NR^5$—$C(O)R^{10}$, —$OCF_3$, —$CF_3$, $C_1$-$C_6$-alkyl, or (iii) a $C_3$-$C_8$ cycloalkyl or heterocyclyl ring having 3 to 8 ring atoms and optionally identically or differently mono- or polysubstituted by hydroxyl, —$NR^6R^7$, cyano, halogen, $C_1$-$C_6$-alkoxy, —$OCF_3$, —$CF_3$, $C_1$-$C_6$-alkyl, $R^2$ represents hydrogen, halogen, cyano, —$C(O)OR^{10}$, —$C(O)OH$, —$C(O)NR^6R^7$ or a $C_1$-$C_6$-alkyl or $C_1$-$C_6$-alkoxy radical optionally identically or differently mono- or polysubstituted by halogen, hydroxyl, $C_1$-$C_6$-alkoxy, —$CF_3$, —$OCF_3$ or —$NR^6R^7$, R³ represents a $C_1$-$C_6$-alkyl radical or a $C_3$-$C_7$-cycloalkyl ring, optionally itself identically or differently mono- or polysubstituted by hydroxyl, —C(O)OR¹⁰, —C(O)NR⁶R⁷, —NR⁶R⁷, cyano, halogen, —CF₃, $C_1$-$C_6$-alkoxy, —OCF₃ and/or $C_1$-$C_6$-alkyl, X represents the group —NR⁴—, Y represents —O— or the group —NR⁴—, A represents an aryl or heteroaryl ring optionally identically or differently mono- or polysubstituted by hydroxyl, —NR⁶R⁷, —C(O)NR⁶R⁷, cyano, halogen, $C_1$-$C_6$-alkoxy, —OCF₃, —CF₃, $C_1$-$C_6$-alkyl, $C_3$-$C_6$-cycloalkyl and/or heterocyclyl having 3 to 8 ring atoms, n represents 1-5, R⁴ represents
hydrogen, a $C_1$-$C_6$-alkyl radical, a $C_3$-$C_8$-cycloalkyl ring or —C(O)—($C_1$-$C_6$)-alkyl, are in each case optionally identically or differently mono- or polysubstituted by hydroxyl, —NR⁸R⁹, cyano, halogen, —CF₃, $C_1$-$C_6$-alkoxy and/or —OCF₃, R⁵ represents hydrogen or a $C_1$-$C_6$-alkyl radical, R⁶ and R⁷ independently of one another represent
(i) hydrogen and/or
(ii) a $C_1$-$C_6$-alkyl radical, a $C_3$-$C_8$-cycloalkyl and/or aryl ring, a heterocyclyl ring having 3 to 8 ring atoms and/or a heteroaryl ring, are optionally identically or differently mono- or polysubstituted by hydroxyl, —NR⁸R⁹, cyano, halogen, —CF₃, $C_1$-$C_6$-alkoxy and/or —OCF₃, R⁸ and R⁹ independently of one another represent hydrogen or a $C_1$-$C_3$-alkyl radical, R¹⁰ represents a $C_1$-$C_3$-alkyl, a $C_3$-$C_8$-cycloalkyl or aryl ring, a heterocyclyl ring having 3 to 8 ring atoms or a heteroaryl ring, in each case optionally itself identically or differently mono- or polysubstituted by hydroxyl, halogen, cyano, nitro, —NR⁶R⁷, $C_1$-$C_6$-alkyl —CF₃, $C_1$-$C_6$-alkoxy and/or —OCF₃, and their salts, diastereomers and enantiomers.

Compounds of the general formula (1) form a more preferred subgroup, in which

R¹ represents a heteroaryl ring optionally substituted by hydroxyl, or represents a $C_1$-$C_6$-alkyl radical or $C_3$-$C_8$ cycloalkyl ring optionally identically or differently mono- or polysubstituted by —NR⁶R⁷ or $C_1$-$C_6$-alkoxy R² represents hydrogen, halogen, —C(O)OR¹⁰, —C(O)OH or a $C_1$-$C_6$-alkoxy radical, R³ represents a $C_1$-$C_6$-alkyl radical X represents —NH—, Y represents —O—, A represents an aryl ring, n represents 1-4, R⁶ and R⁷ independently of one another represent hydrogen or a $C_1$-$C_6$-alkyl radical R¹⁰ represents a $C_1$-$C_3$-alkyl radical or an aryl ring, in each case optionally itself substituted by nitro, and their salts, diastereomers and enantiomers.

Compounds of the general formula (1) form a likewise more preferred subgroup, in which R¹ represents
(i) a monocyclic heteroaryl ring optionally identically or differently mono- or polysubstituted by hydroxyl, —NR⁵—C(O)—R¹⁰, cyano, $C_1$-$C_6$-alkyl, or
(ii) a $C_1$-$C_6$-alkyl radical optionally identically or differently mono or polysubstituted by hydroxyl, —NR⁶R⁷ $C_1$-$C_6$-alkoxy and/or $C_3$-$C_6$-cycloalkyl, or
(iii) a $C_3$-$C_8$ cycloalkyl ring.

R² represents hydrogen, halogen, cyano, —C(O)OR¹⁰, —C(O)OH, or a $C_1$-$C_6$-alkoxy radical, R³ represents a $C_1$-$C_6$-alkyl radical X represents —NH—, Y represents —O—, or —NH—

A represents a phenyl or monocyclic heteroaryl ring, n represents 1-4,

R⁵ represents hydrogen,

R⁶ and R⁷ independently of one another represent hydrogen or a $C_1$-$C_6$-alkyl radical, and R¹⁰ represents a $C_1$-$C_6$-alkyl radical or phenyl ring, in each case optionally itself substituted by nitro, and their salts, diastereomers and enantiomers.

The compounds of the general formula (I) form a particularly preferred subgroup, in which R¹ represents a $C_1$-$C_6$-alkyl radical optionally identically or differently mono- or polysubstituted by hydroxyl, —NR⁶R⁷, $C_1$-$C_6$-alkoxy and/or $C_3$-$C_6$-cycloalkyl, R² represents hydrogen, halogen, cyano or a $C_1$-$C_6$-alkoxy radical, R³ represents a $C_1$-$C_6$-alkyl radical X represents —NH—, Y represents —O— or —NH—, A represents a phenyl or monocyclic heteroaryl ring, n represents 1 or 2, and R⁶ and R⁷ independently of one another represent hydrogen or a $C_1$-$C_3$-alkyl radical, and their salts, diastereomers and enantiomers.

The compounds of the general formula (I) form an extremely preferred subgroup, in which R¹ represents a $C_1$-$C_3$-alkyl radical, R² represents halogen or a $C_1$-$C_6$-alkoxy radical, R³ represents a $C_1$-$C_3$-alkyl radical, X represents —NH—, Y represents —O—, A represents a phenyl ring, and n represents 1, and their salts, diastereomers and enantiomers.

In the general formula (I), R¹ can represent
(i) an aryl or heteroaryl ring optionally identically or differently mono- or polysubstituted by hydroxyl, —NR⁶R⁷, —NR⁵—C(O)—R¹⁰, —NR⁵—C(O)—OR¹⁰, —NR⁵—C(O)—NR⁶R⁷, —NR⁶—SO₂—R¹⁰, cyano, halogen, $C_1$-$C_6$-alkoxy, —OCF₃, —CF₃, $C_1$-$C_6$-alkyl, $C_3$-$C_6$-cycloalkyl and/or heterocyclyl having 3 to 8 ring atoms, or
(ii) a $C_1$-$C_6$-alkyl, $C_2$-$C_6$-alkenyl or $C_2$-$C_6$-alkynyl radical, optionally identically or differently mono- or polysubstituted by hydroxyl, —NR⁶R⁷, —NR⁵—C(O)R¹⁰, —NR⁵—C(O)—OR¹⁰, —NR⁵—C(O)—NR⁶R⁷, —NR⁵—SO₂—R¹⁰, cyano, halogen, $C_1$-$C_6$-alkoxy, —OCF₃, —CF₃, $C_1$-$C_6$-alkyl, $C_3$-$C_6$-cycloalkyl and/or heterocyclyl having 3 to 8 ring atoms, or
(iii) a $C_3$-$C_8$ cycloalkyl or heterocyclyl ring having 3 to 8 ring atoms and optionally identically or differently mono- or polysubstituted by hydroxyl, —NR⁶R⁷, —NR⁵—C(O)—R¹⁰, —NR⁵—C(O)—OR¹⁰, —NR⁵—C(O)—NR⁶R⁷, —NR⁵—SO₂—R¹⁰, cyano, halogen, $C_1$-$C_6$-alkoxy, —OCF₃, —CF₃, $C_1$-$C_6$-alkyl, $C_3$-$C_6$-cycloalkyl and/or heterocyclyl having 3 to 8 ring atoms.

Preferably, R¹ represents
(i) a heteroaryl ring optionally identically or differently mono- or polysubstituted by hydroxyl, —NR⁶R⁷, cyano, halogen, $C_1$-$C_6$-alkoxy, —NR⁵—C(O)R¹⁰, —OCF₃, —CF₃, $C_1$-$C_6$-alkyl, or (ii) a $C_1$-$C_6$-alkyl radical optionally identically or differently mono- or polysubstituted by hydroxyl, —$NR^6R^7$, cyano, halogen, $C_1$-$C_6$-alkoxy, —$NR^5$—$C(O)R^{10}$, —$OCF_3$, —$CF_3$, $C_1$-$C_6$-alkyl, or (iii) a $C_3$-$C_8$ cycloalkyl or heterocyclyl ring having 3 to 8 ring atoms and optionally identically or differently mono- or polysubstituted by hydroxyl, —$NR^6R^7$, cyano, halogen, $C_1$-$C_6$-alkoxy, —$OCF_3$, —$CF_3$, $C_1$-$C_6$-alkyl.

More preferably, $R^1$ represents:

(i) a monocyclic heteroaryl ring optionally identically or differently mono- or polysubstituted by hydroxyl, —$NR^5$—$C(O)$—$R^{10}$, cyano, $C_1$-$C_6$-alkyl, or (ii) a $C_1$-$C_6$-alkyl radical optionally identically or differently mono- or polysubstituted by hydroxyl, —$NR^6R^7$, $C_1$-$C_6$-alkoxy and/or $C_3$-$C_6$-cycloalkyl, or (iii) a $C_3$-$C_8$ cycloalkyl ring.

Likewise more preferably, $R^1$ also represents:

a heteroaryl ring optionally substituted by hydroxyl, or a $C_1$-$C_6$-alkyl radical or $C_3$-$C_8$ cycloalkyl ring optionally identically or differently mono- or polysubstituted by —$NR^6R^7$ or $C_1$-$C_6$-alkoxy.

Particularly preferably, $R^1$ represents a $C_1$-$C_6$-alkyl radical optionally identically or differently mono- or polysubstituted by hydroxyl, —$NR^6R^7$, $C_1$-$C_6$-alkoxy and/or $C_3$-$C_6$-cycloalkyl, where $R^6$ and $R^7$ independently of each other represent hydrogen or a $C_1$-$C_3$ alkyl radical.

Extremely preferably, $R^1$ represents a $C_1$-$C_3$ alkyl radical.

In the general formula (I), $R^2$ can represent (i) hydrogen, (ii) hydroxyl, halogen, cyano, nitro, —$CF_3$, —$OCF_3$, —$C(O)OR^{10}$, —$C(O)OH$, —$C(O)NR^6R^7$, —$C(S)NR^6R^7$, —$NR^6R^7$, —$NR^5$—$C(O)$—$R^{10}$, —$NR^5$—$C(O)$—$OR^{10}$, —$NR^5$—$C(O)$—$NR^6R^7$, —$NR^5$—$SO_2$—$R^{10}$, or (iii) a $C_1$-$C_6$-alkyl or $C_1$-$C_6$-alkoxy radical optionally identically or differently mono- or polysubstituted by halogen, hydroxyl, $C_1$-$C_6$-alkoxy, —$CF_3$, —$OCF_3$ or —$NR^6R^7$, or (iv) a $C_3$-$C_8$-cycloalkyl ring optionally identically or differently mono- or polysubstituted by halogen, hydroxyl, $C_1$-$C_6$-alkoxy, —$CF_3$, —$OCF_3$, —$NR^6R^7$ and/or $C_1$-$C_6$-alkyl.

Preferably, $R^2$ represents:

hydrogen, halogen, cyano, —$C(O)OR^{10}$, —$C(O)OH$, —$C(O)NR^6R^7$ or a $C_1$-$C_6$-alkyl or $C_1$-$C_6$-alkoxy radical optionally identically or differently mono- or polysubstituted by halogen, hydroxyl, $C_1$-$C_6$-alkoxy, —$CF_3$, —$OCF_3$ or —$NR^6R^7$.

More preferably, $R^2$ represents:

hydrogen, halogen, cyano, —$C(O)OR^{10}$, —$C(O)OH$ or a $C_1$-$C_6$-alkoxy radical.

More preferably, $R^2$ also represents hydrogen, halogen, —$C(O)OR^{10}$, —$C(O)OH$ or a $C_1$-$C_6$-alkoxy radical.

Particularly preferably, $R^2$ represents hydrogen, halogen, cyano or a $C_1$-$C_6$-alkoxy radical.

Extremely preferably, $R^2$ represents halogen or a $C_1$-$C_6$-alkoxy radical.

In the general formula (I), $R^3$ can represent a $C_1$-$C_6$-alkyl, $C_2$-$C_6$-alkenyl or $C_2$-$C_6$-alkynyl radical, a $C_3$-$C_7$-cycloalkyl or aryl ring, a heterocyclyl ring having 3 to 8 ring atoms or a monocyclic heteroaryl ring, in each case optionally itself identically or differently mono- or polysubstituted by hydroxyl, —$C(O)OR^{10}$, —$C(O)NR^6R^7$, —$NR^6R^7$, cyano, halogen, —$CF_3$, $C_1$-$C_6$-alkoxy, —$OCF_3$ and/or $C_1$-$C_6$-alkyl.

Preferably, $R^3$ represents a $C_1$-$C_6$-alkyl radical or a $C_3$-$C_7$-cycloalkyl ring, optionally itself identically or differently mono- or polysubstituted by hydroxyl, —$C(O)OR^{10}$, —$C(O)NR^6R^7$, —$NR^6R^7$, cyano, halogen, —$CF_3$, $C_1$-$C_6$-alkoxy, —$OCF_3$ and/or $C_1$-$C_6$-alkyl.

Particularly preferably, $R^3$ represents a $C_1$-$C_6$-alkyl radical.

Extremely preferably, $R^3$ represents a $C_1$-$C_3$-alkyl radical

In the general formula (I), X and Y independently of one another represent: —O— or the group —$NR^4$—.

Preferably, X represents the group —$NR^4$—.

Particularly preferably, X represents —NH—.

Preferably, Y represents the group —$NR^4$—.

Particularly preferably, Y represents —O— or —NH—.

Exceptionally preferably, Y represents —O—.

In the general formula (I), A can represent an aryl or heteroaryl ring optionally identically or differently mono- or polysubstituted by hydroxyl, —$NR^6R^7$, —$NR^5$—$C(O)$—$R^{10}$, —$C(O)NR^6R^7$, —$NR^5$—$C(O)$—$OR^{10}$, —$NR^5$—$C(O)$—$NR^6R^7$, —$NR^5$—$SO_2$—$R^{10}$, cyano, halogen, $C_1$-$C_6$-alkoxy, —$OCF_3$, —$CF_3$, $C_1$-$C_6$-alkyl, $C_3$-$C_6$-cycloalkyl and/or heterocyclyl having 3 to 8 ring atoms.

Preferably, A represents:

an aryl or heteroaryl ring optionally identically or differently mono- or polysubstituted by hydroxyl, —$NR^6R^7$, —$C(O)NR^6R^7$, cyano, halogen, $C_1$-$C_6$-alkoxy, —$OCF_3$, —$CF_3$, $C_1$-$C_6$-alkyl, $C_3$-$C_6$-cycloalkyl and/or heterocyclyl having 3 to 8 ring atoms.

More preferably, A represents an aryl ring.

Particularly preferably, A represents a phenyl or monocyclic heteroaryl ring.

Extremely preferably, A represents a phenyl ring.

In the general formula (I), n can represent 1-6.

Preferably, n represents 1-5.

More preferably, n represents 1-4.

Particularly preferably, n represents 1 or 2.

Extremely preferably, n represents 1.

In the general formula (I), $R^4$ can represent (i) hydrogen, (ii) a $C_1$-$C_6$-alkyl radical, $C_3$-$C_8$-cycloalkyl or aryl ring, a heterocyclyl ring having 3 to 8 ring atoms or a heteroaryl ring, or (iii) —$C(O)$—$(C_1$-$C_6)$-alkyl, —$C(O)$-phenyl, or —$C(O)$-benzyl, where (ii) and (iii) are optionally identically or differently mono- or polysubstituted by hydroxyl, —$NR^8R^9$, cyano, halogen, —$CF_3$, $C_1$-$C_6$-alkoxy and/or —$OCF_3$, or, if X represents —$NR^4$—, alternatively X, $R^1$ and $R^4$ together form a 3- to 8-membered ring which optionally, in addition to the nitrogen atom, contains one or more further heteroatoms, is optionally identically or differently mono- or polysubstituted by hydroxyl, $C_1$-$C_6$-alkyl, $C_1$-$C_6$-alkoxy, —$C(O)R^{10}$, —$SO_2R^{10}$, halogen or the group —$NR^8R^9$, optionally contains 1 to 3 double bonds and/or is optionally interrupted by one or more —$C(O)$— groups, Preferably, $R^4$ represents:

hydrogen, a $C_1$-$C_6$-alkyl radical, a $C_3$-$C_8$-cycloalkyl ring or —$C(O)$—$(C_1$-$C_6)$-alkyl, are in each case optionally identically or differently mono- or polysubstituted by hydroxyl, —$NR^8R^9$, cyano, halogen, —$CF_3$, $C_1$-$C_6$-alkoxy and/or —$OCF_3$.

Particularly preferably, $R^4$ represents hydrogen.

In the general formula (I), $R^5$ can represent
hydrogen or a $C_1$-$C_6$-alkyl radical.

Preferably, $R^5$ represents hydrogen or a $C_1$-$C_3$-alkyl radical.

Particularly preferably, $R^5$ represents hydrogen.

In the general formula (1), $R^6$ and $R^7$ independently of one another can represent
(i) hydrogen and/or
(ii) a $C_1$-$C_6$-alkyl radical, $C_2$-$C_6$-alkenyl, $C_3$-$C_8$-cycloalkyl and/or aryl ring, a heterocyclyl ring having 3 to 8 ring atoms and/or a heteroaryl ring, are optionally identically or differently mono- or polysubstituted by hydroxyl, —$NR^8R^9$, cyano, halogen, —$CF_3$, $C_1$-$C_6$-alkoxy and/or —$OCF_3$, or $R^6$ and $R^7$ together with the nitrogen atom form a 5- to 7-membered ring, which optionally in addition to the nitrogen atom contains 1 or 2 further heteroatoms and which can be identically or differently mono- or polysubstituted by hydroxyl, —$NR^8R^9$, cyano, halogen, —$CF_3$, $C_1$-$C_6$-alkyl, $C_1$-$C_6$-alkoxy and/or —$OCF_3$.

Preferably, $R^6$ and $R^7$ independently of one another represent:
(i) hydrogen and/or
(ii) a $C_1$-$C_6$-alkyl radical, a $C_3$-$C_8$-cycloalkyl and/or aryl ring, a heterocyclyl ring having 3 to 8 ring atoms and/or a heteroaryl ring,
are optionally identically or differently mono- or polysubstituted by hydroxyl, —$NR^8R^9$, cyano, halogen, —CF $C_1$-$C_6$-alkoxy and/or —$OCF_3$.

Particularly preferably, $R^6$ and $R^7$ independently of one another represent: hydrogen or a $C_1$-$C_6$-alkyl radical.

Extremely preferably, $R^6$ and $R^7$ independently of one another represent: hydrogen or a $C_1$-$C_3$-alkyl radical.

In the general formula (I), $R^8$ and $R^9$ independently of one another represent:
hydrogen or a $C_1$-$C_6$-alkyl radical, which is optionally identically or differently mono- or polysubstituted by hydroxyl or halogen.

Preferably, $R^8$ and $R^9$ independently of one another represent hydrogen or a $C_1$-$C_3$-alkyl radical.

In the general formula (I), $R^{10}$ can represent
for a $C_1$-$C_6$-alkyl, $C_2$-$C_6$-alkenyl or $C_2$-$C_6$-alkynyl radical, a $C_3$-$C_8$-cycloalkyl or aryl ring, a heterocyclyl ring having 3 to 8 ring atoms or a heteroaryl ring, in each case optionally itself identically or differently mono- or polysubstituted by hydroxyl, halogen, cyano, nitro, —$NR^6R^7$, $C_1$-$C_6$-alkyl ,—$CF_3$, $C_1$-$C_6$-alkoxy and/or —$OCF_3$.

Preferably, $R^{10}$ represents
a $C_1$-$C_3$-alkyl, a $C_3$-$C_8$-cycloalkyl or aryl ring, a heterocyclyl ring having 3 to 8 ring atoms or a heteroaryl ring,
in each case optionally itself identically or differently mono- or polysubstituted by hydroxyl, halogen, cyano, nitro, —$NR^6R^7$, $C_1$-$C_6$-alkyl ,—$CF_3$, $C_1$-$C_6$-alkoxy and/or —$OCF_3$.

Particularly preferably, $R^{10}$ represents:
for a $C_1$-$C_6$-alkyl radical or a phenyl ring, in each case optionally itself substituted by nitro.

Likewise particularly preferably, $R^{10}$ represents:
a $C_1$-$C_3$-alkyl radical or an aryl ring, in each case optionally itself substituted by nitro. All compounds which result by any possible combination of the abovementioned possible, preferred and particularly preferred meanings of the substituents are likewise to be regarded as covered by the present invention.

Particular embodiments of the invention moreover consist in compounds which result by combination of the meanings for the substituents directly disclosed in the examples.

The salts of the compounds are likewise to be regarded as covered by the present invention.

The formulation of the compounds according to the invention to give pharmaceutical preparations is carried out in a manner known per se, by converting the active compound or compounds into the desired administration form using the excipients customary in galenics.

Excipients which can be used here are, for example, vehicles, fillers, disintegrants, binders, moisturizers, lubricants, absorbents and adsorbents, diluents, solvents, cosolvents, emulsifiers, solubilizers, taste corrigents, colourants, preservatives, stabilizers, wetting agents, salts for changing the osmotic pressure or buffers. Reference is to be made here to Remington's Pharmaceutical Science, 15th ed. Mack Publishing Company, East Pennsylvania (1980).

The pharmaceutical formulations can be present
in solid form, for example as tablets, coated tablets, pills, suppositories, capsules, transdermal systems or
in semi-solid form, for example as ointments, creams, gels, suppositories, emulsions or
in liquid form, for example as solutions, tinctures, suspensions or emulsions.

Excipients within the meaning of the invention can be, for example, salts, saccharides (mono-, di-, tri-, oligo-, and/or polysaccharides), proteins, amino acids, peptides, fats, waxes, oils, hydrocarbons and their derivatives, where the excipients can be of natural origin or can be obtained synthetically or partially synthetically.

Tablets, coated tablets, capsules, pills, powders, granules, pastilles, suspensions, emulsions or solutions, in particular, are suitable for oral or peroral administration. Suspensions, emulsions and especially solutions, in particular, are suitable for parenteral administration.

On account of their anti-inflammatory and in addition immunosuppressive action, the compounds of the general formula (I) according to the invention can be used for local and systemic administration as medicaments for the treatment or prophylaxis of the following disease states in mammals and humans:
(i) Pulmonary diseases which involve inflammatory, allergic and/or proliferative processes:
Chronic obstructive pulmonary diseases of any genesis, especially bronchial asthma
Bronchitis of varying genesis
Adult respiratory distress syndrome (ARDS), acute respiratory distress syndrome
Bronchiectasis
All forms of restrictive pulmonary diseases, especially allergic alveolitis,
Pulmonary oedema, in particular allergic
Sarcoidosis and granulomatosis, in particular Boeck disease
(ii) Rheumatic diseases/autoimmune diseases/joint diseases, which involve inflammatory, allergic and/or proliferative processes:
All forms of rheumatic diseases, in particular rheumatoid arthritis, acute rheumatic fever, rheumatic polymyalgia, Behcet's disease
Reactive arthritis
Inflammatory soft-tissue diseases of other genesis
Arthritic symptoms in degenerative joint diseases (arthroses)
Vitiligo Collagenoses of any origin, e.g. systemic lupus erythematosus, scleroderma, polymyositis, dermatomyositis-Sjögren's syndrome, Stilt's disease, Felty's syndrome Sarcoidoses and granulomatoses Soft tissue rheumatism (iii) Allergies or pseudoallergic diseases, which involve inflammatory, and/or proliferative processes:

All forms of allergic reactions, e.g. Quincke's oedema, hayfever, insect bite, allergic reactions to medicaments, blood derivatives, contrast agents etc., anaphylactic shock urticaria, allergic and irritative contact dermatitis, allergic vascular diseases Allergic vasculitis (iv) Vascular inflammation (vasculitis)

Panarteritis nodosa, temporal arteritis, nodal fever

Polyarteritis nodosa

Wegener's granulomatosis

Giant cell arteritis (v) Dermatological diseases which involve inflammatory, allergic and/or proliferative processes:

Atopic dermatitis (especially in children)

All forms of eczema such as, for example, atopic eczema (esp. in children)

Exanthema of any genesis or dermatoses

Psoriasis and parapsoriasis disorder

Pityriasis rubra pilaris

Erythematous diseases caused by different noxae, e.g. rays, chemicals, burns etc.

Bullous dermatoses such as, for example, autoimmune pemphigus vulgaris, bullous pemphigoid Diseases of the lichenoid type, Pruritus (e.g. of allergic genesis)

Rosacea disorder

Stevens-Johnson syndrome

Manifestation of vascular diseases

Hair loss such as alopecia areata

Cutaneous lymphoma (vi) Renal diseases which involve inflammatory, allergic and/or proliferative processes:

Nephrotic syndrome

All nephrites, e.g. glomerulonephritis (vii) Hepatic diseases which involve inflammatory, allergic and/or proliferative processes:

acute hepatitis of varying origin chronic aggressive and/or chronic intermittent hepatitis (viii) Gastrointestinal diseases which involve inflammatory, allergic and/or proliferative processes:

regional enteritis (Crohn's disease)

ulcerative colitis gastroenteritis of varying origin, e.g. endemic sprue (ix) Eye diseases which involve inflammatory, allergic and/or proliferative processes:

allergic keratitis, uveitis, iritis, conjunctivitis blepharitis optical nerve neuritis chorioiditis sympathetic ophthalmia (x) Diseases of the otorhinolaryngological region, which involve inflammatory, allergic and/or proliferative processes:

allergic rhinitis hayfever external otitis, e.g. caused by contact eczeme (xi) neurological diseases which involve inflammatory, allergic and/or proliferative processes:

cerebral oedema, especially allergic cerebral oedema multiple sclerosis acute encephalomyelitis meningitis, especially allergic Guillain-Barre syndrome Alzheimer's disease (xii) Blood diseases which involve inflammatory, allergic and/or proliferative processes, such as, for example: Hodgkin's disease or non-Hodgkin's lymphoma, thrombocytaemias, erythrocytoses Acquired haemolytic anaemia Idiopathic thrombocytopenia Idiopathic granulocytopenia (xiii) Oncoses which involve inflammatory, allergic and/or proliferative processes Acute lymphatic leukaemia Malignant lymphoma Lymphogranulomatoses Lymphosarcomas (xiv) Endocrine diseases which involve inflammatory, allergic and/or proliferative processes such as, for example:

Endocrine orbitopathy

De Quervain thyroiditis

Hashimoto's thyroiditis

Basedow's disease

Granulomatous thyroiditis

Lymphadenoid goitre

Autoimmune adrenalitis

Diabetes mellitus, in particular type 1 diabetes

Endometriosis (xv) Organ and tissue transplants, graft-versus-host disease (xvi) Severe states of shock, e.g. anaphylactic shock, systemic inflammatory response syndrome (SIRS)

One subject of the invention is the use of the compounds of the general formula (I) according to the invention for the production of a medicament.

A further subject of the invention is the use of the compounds according to the invention for the treatment of diseases which involve inflammatory, allergic and/or proliferative processes.

Preparation of the Compounds According to the Invention

Process Variant 1:

Scheme 1

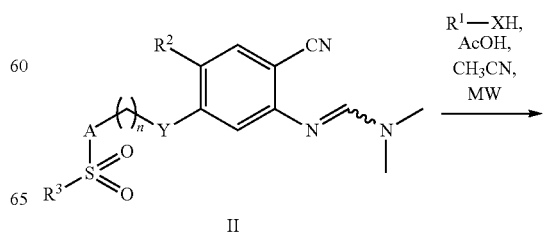

II

Preparation of the Intermediates of the Formula (III)

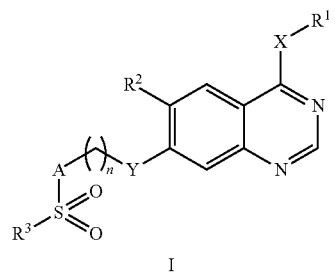

I

According to Y. Hang et al. (Org. Lett, 2004, 6, 4775-4778), the preparation of the compounds of the general formula (I) according to the invention is carried out by reaction of the intermediates as in formula (II) with compounds $R^1$—XH in the presence of acetic acid in acetonitrile as a solvent in a microwave, where $R^1$, $R^2$, $R^3$ and X, Y A and n have the meanings indicated in the general formula (I) according to Claims 1 to 11.

Preparation of the Intermediates of the Formula (II):

Scheme 2

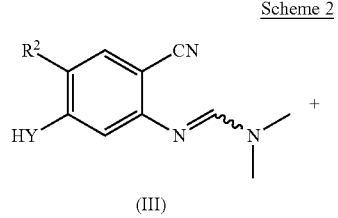

(III)

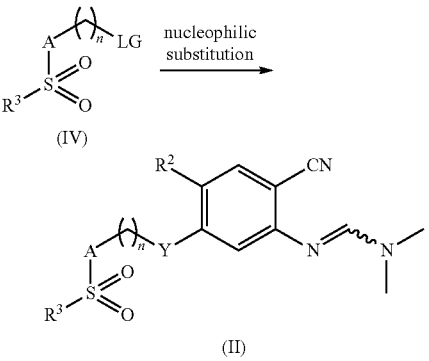

The substituents $R^2$, $R^3$ and Y, A and n have the meanings indicated in the general formula (I) according to Claims 1 to 11.

Intermediates of the formula (II) are obtained by a nucleophilic substitution reaction of intermediates of the formula (III) with intermediates of the formula (IV). Intermediates of the formula (IV) are functionalized here using a group LG suitable for this purpose. Halogen and a mesylate, tosylate or triflate group, for example, are suitable as an LG. For the reaction of the intermediates (III) with (IV), inter alia, sodium carbonate, potassium carbonate or caesium carbonate are used as a base. Suitable solvents are, for example, acetone or dimethylformamide.

Scheme 3

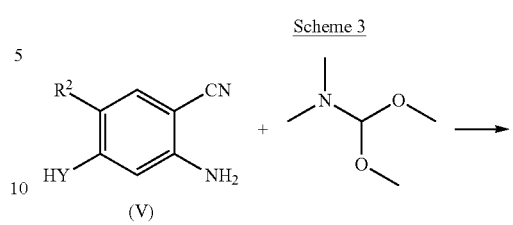

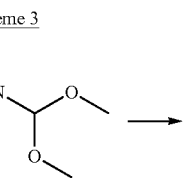

(III)

Intermediates of the formula (III) are obtained by reaction of intermediates of the formula (V) with N,N-dimethylformamide dimethyl acetal, where $R^2$ and Y have the meanings indicated in the general formula (I) according to Claims 1 to 11.

Preparation of the Intermediates of the Formula (IV)

Scheme 4

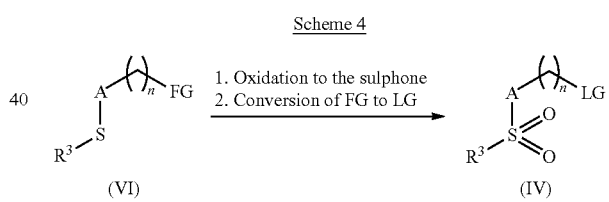

(VI)                                                           (IV)

1. Oxidation to the Sulphone.

A thioether of the formula (VI) is initially converted to the corresponding sulphone compound, where A and $R^3$ have the meanings indicated in the general formula (I) according to Claims 1 to 11. Suitable oxidizing agents for this transformation are, for example, sodium periodate, meta-chloroperbenzoic acid, hydrogen peroxide or potassium peroxomonosulphate. The oxidation to the sulphone is dropped when the corresponding sulphone compound is already commercially available.

2. Conversion of FG to LG

Functional groups FG are, for example, carboxylic acid and ester. These groups can be reduced to the corresponding alcohol. In a subsequent step, the alcohol is converted to a mesylate, tosylate and triflate group belonging too the LG group.

If A=aryl/hetaryl and n=1, FG can be, for example, a hydroxyl group or hydrogen optionally present in protected form. By means of free radical halogenation, this hydrogen can be replaced by a halogen substituent.

Process Variant 2:

Scheme 5

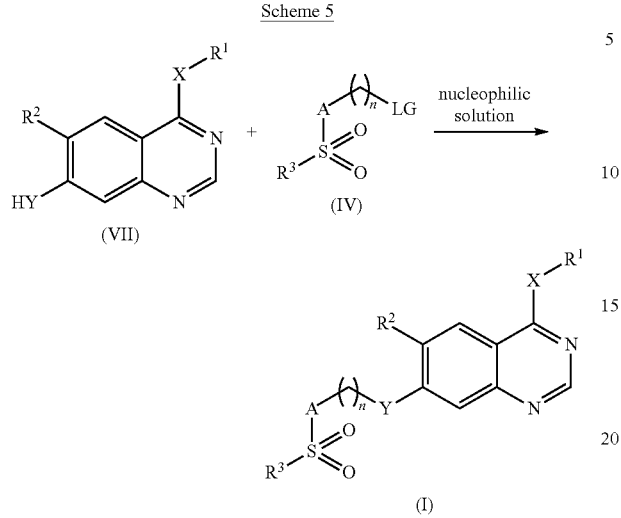

The preparation of the compounds of the general formula (I) according to the invention is carried out in this variant by the reaction of the quinazolines of the formula (VII) with intermediates of the formula (IV), where $R^1$, $R^2$, $R^3$ and X, Y, A and n have the meanings indicated in the general formula (I) according to Claims 1 to 11. The reaction is carried out analogously to the reaction of the intermediates of the formula (III) with intermediates of the formula (IV) (see Scheme 2).

Preparation of the Intermediates of the Formula (VII)

The synthesis of the quinazolines of the (VII) is carried out in a manner analogous to that described in Process variant 1 (see Scheme 1) or according to other methods known to the person skilled in the art (for this see Science of Synthesis, Houben-Weyl Methods of Molecular Transformations, Thieme Verlag, 2004, Volume 16, pages 573-749).

Process Variant 3:

Scheme 6

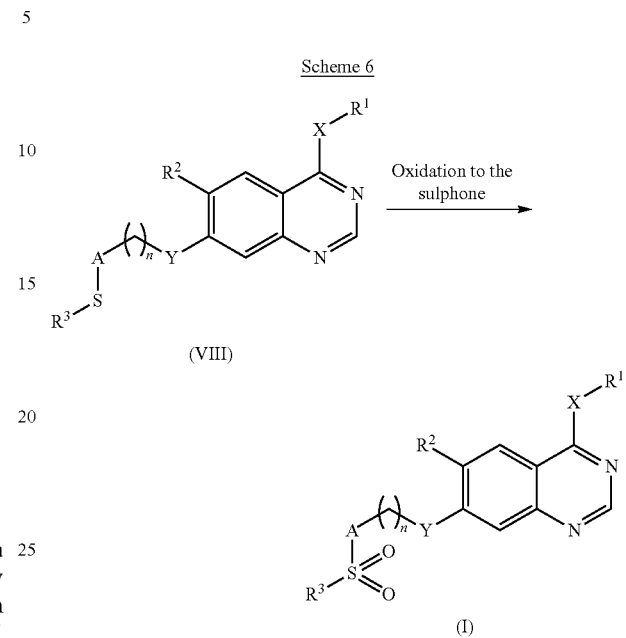

In this process variant, the compounds of the general formula (I) according to the invention can be converted by oxidation, at the sulphur centre, of the compounds of the formula (VIII) to the corresponding sulphone, where $R^1$, $R^2$, $R^3$ and X, Y, A and n have the meanings indicated in the general formula (I) according to Claims 1 to 11.

Preparation of the Intermediates of the Formula (VIII):

Variant VIII-A

Scheme 7

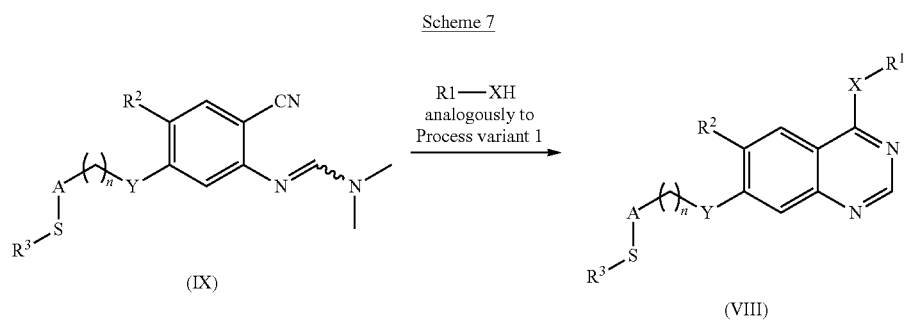

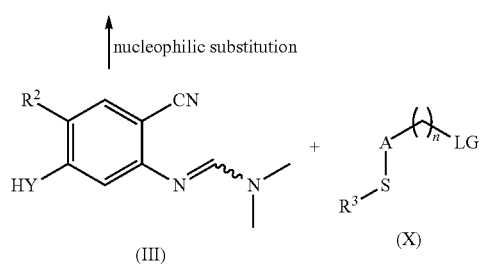

Intermediates of the formula (VIII) can be prepared analogously to Process variant 1 (see Scheme 1). Intermediates of the formula (IX) are obtained analogously to Scheme 3 by, reaction of the intermediates of the formula (III) with intermediates of the formula (X). $R^1$, $R^2$, $R^3$ and X, Y, A and n have the meanings indicated in the general formula (I) according to Claims 1 to 11.

Scheme 8

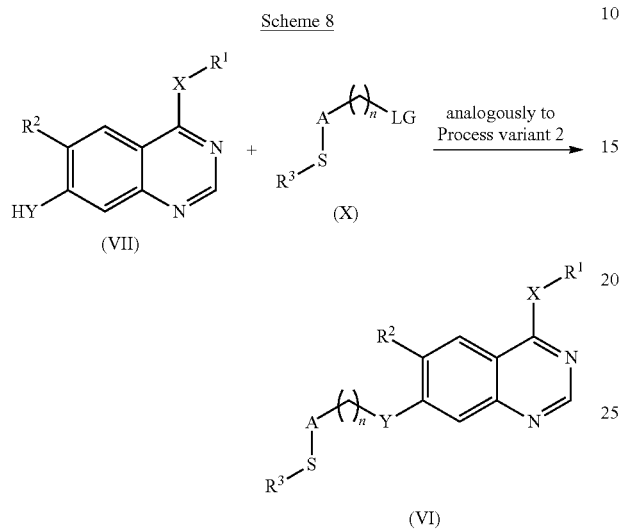

Variant VIII-B

Alternatively and analogously to Process variant 2 (see Scheme 5), intermediates of the formula (VIII) can be prepared by reaction of the intermediates of the formula (VII) with intermediates of the formula (X).

Halogen and a mesylate, tosylate or triflate group and in this case also a hydroxyl group are suitable, for example, as LG.

If LG is a hydroxyl group, the linkage of the intermediates of the formula (V) with intermediates of the formula (X) can be carried out, for example, by means of a Mitsunobu reaction (O. Mitsunobu Synthesis 1981, 1-27).

EXPERIMENTAL SECTION

I. Synthesis
Process Variant 1

Example 1.1

[6-Bromo-7-(3-methanesulphonylbenzyloxy)quinazolin-4-yl]isopropylamine

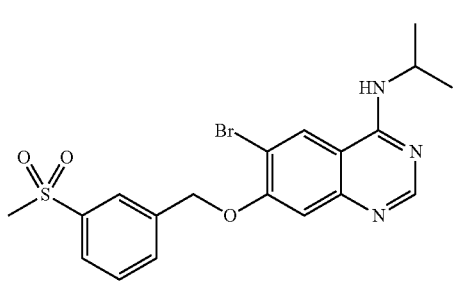 [SMILES: CC(C)Nc1ncnc2cc(OCc3cccc(S(C)(=O)=O)c3)c(Br)cc12]

1.1.a) Preparation of the Intermediates
Compound 1.1.a.1

2-Amino-5-bromo-4-methoxybenzonitrile

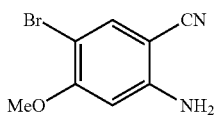

2-Amino-4-methoxybenzonitrile (4.47 g, 30.2 mmol) is dissolved in 70 ml of dioxane and treated at 0° C. with bromine (1.71 ml, 33.2 mmol). It is subsequently stirred at 0° C. for one hour. After addition of diethyl ether, the resulting crystals are filtered off with suction. The desired product is obtained in 81% yield (5.52 g).
$^1$H-NMR (400 MHz, DMSO-d6): δ 3.75 (s, 3H), 6.30-6.50 (m, 3H), 7.54 (s, 1H).
Compound 1.1.a.2

(E/Z)-N'-(4-Bromo-2-cyano-5-methoxyphenyl)-N,N-dimethylformimidamide

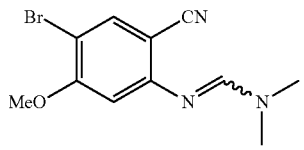 [SMILES: COc1cc(N=CN(C)C)c(C#N)cc1Br]

2-Amino-5-bromo-4-methoxybenzonitrile (3.0 g, 13.2 mmol) is treated with N,N-di-methylformamide dimethyl acetal (6.5 ml, 48.9 mmol) and subsequently stirred at room temperature for 24 hours. The reaction mixture is concentrated to dryness a number of times with toluene. The desired product is obtained after chromatographic purification (silica gel, hexane/ethyl acetate: 0→100% ethyl acetate, then ethyl acetate/methanol: 4/1) in 42% yield (1.56 g).
$^1$H-NMR (300 MHz, DMSO-d6): δ 2.95 (s, 3H), 3.05 (s, 3H), 3.87 (s, 3H), 6.80 (s, 1H), 7.75 (s, 1H), 7.99 (s, 1H).
Compound 1.1.a.3

(E/Z)-N'-(4-Bromo-2-cyano-5-hydroxyphenyl)-N,N-dimethylformimidamide

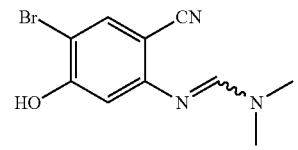

(E/Z)-N'-(4-Bromo-2-cyano-5-methoxyphenyl)-N,N-dimethylformimidamide (1.28 g, 4.54 mmol) is dissolved in 45 ml of methylene chloride. Boron tribromide solution (1 M) in methylene chloride (91 ml, 91 mmol) is added dropwise. After 20 hours at room temperature, the reaction is terminated by addition of methanol. The reaction mixture is concentrated to dryness a number of times with toluene. The desired product is obtained after chromatographic purification (silica gel, hexane/ethyl acetate: 0→100% ethyl acetate, then ethyl acetate/methanol: 4/1) in 21% yield (250 mg).

¹H-NMR (300 MHz, DMSO-d6): δ 2.92 (s, 3H), 3.02 (s, 3H), 6.50 (s, 1H), 7.69 (s, 1H), 7.75 (s, 1H), 11.01 (br, 1H).

Compound 1.1.a.4

(E/Z)-N'-[2-Cyano-5-(3-methanesulphonylbenzyloxy)-4-bromophenyl]-N,N-dimethylformamidine

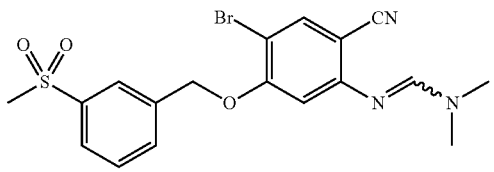

A solution of 1.0 g of 3-methanesulphonyltoluene in 5.9 ml of tetrachloromethane was admixed with 1.05 g of N-bromosuccinimide 11.8 mg of 2,2'-azoisobutyronitrile at 25° C. and subsequently refluxed for 5 hours. After decanting the orange precipitate was washed with tetrachloromethane and the combined organic phases were concentrated under reduced pressure. The 3-bromomethylphenyl methyl sulphone thus obtained was used in the next stage without further clarification. 100 mg of (E/Z)-N'-(4-bromo-2-cyano-5-hydroxyphenyl)-N,N-dimethylformimidamide are suspended in 1.5 ml of acetone together with the bromide freshly prepared above and after admixture of 95.4 mg of potassium carbonate refluxed for 3 hours. After cooling to 25° C., the reaction mixture was admixed with 25 ml of water and washed twice with 25 ml of ethyl acetate each time. The combined organic phases were washed with 25 ml of saturated sodium chloride solution, dried over sodium sulphate and, after filtration, concentrated under reduced pressure. The residue thus obtained was purified by column chromatography on silica gel with ethyl acetate to obtain 166 mg of (E/Z)-N'-[2-Cyano-5-(3-methanesulphonylbenzyloxy)-4-bromophenyl]-N,N-dimethylformamidine.

¹H-NMR (400 MHz), DMSO-d6): δ 2.38/2.67 (s, 3H), 2.96/3.07 (3H), 3.17/3.21 (s, 3H), 4.61/5.36 (s, 2H), 6.96 (s) and 7.48-8.07 (m, 7H).

1.1 b) Preparation of the Final Product 166 mg of the intermediate prepared under 2a) were dissolved in 0.37 ml of acetonitrile. Addition of 0.12 ml of glacial acetic acid and 0.04 ml of isopropylamine was followed by heating in the microwave at 160° C. for 20 minutes. The reaction mixture was admixed with 40 ml of dilute sodium bicarbonate solution and washed three times with 30 ml of ethyl acetate each time. The combined organic phases were dried over sodium sulphate and, after filtration, concentrated under reduced pressure. The residue thus obtained was purified by column chromatography on silica gel with ethyl acetate/0-1% methanol to obtain 79 mg of [6-bromo-7-(3-methanesulphonylbenzyloxy)quinazolin-4-yl]isopropylamine.

¹H-NMR (400 MHz, DMSO-d6): δ 1.21 (d, 6H), 3.21 (s, 3H), 4.42 (dsept, 1H), 5.45 (d, 2H), 7.28 (s, 1H), 7.70 (dd, 1H), 7.84 (d, 1H), 7.90 (m, 2H), 8.07 (s, 1H), 8.38 (s, 1H), 8.68 (s, 1H).

Example 1.2

[6-Bromo-7-(3-Methanesulphonylbenzyloxy)quinazolin-4-yl]ethylamine

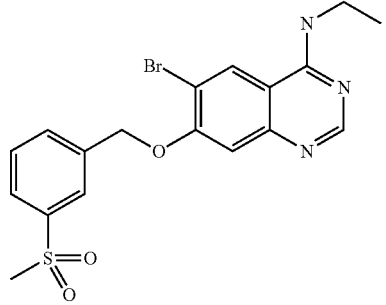 [SMILES: CCNc1ncnc2cc(OCc3cccc(S(C)(=O)=O)c3)c(Br)cc12]

In the same way as for Example 1.1, compound 1.1.a.4 was reacted with ethylamine hydrochloride (yield 70%, colourless crystals).

¹H-NMR (400 MHz, DMSO-d6): δ 1.21 (t, 3H); 3.34 (s, 3H); 3.48-3.57 (m, 2H); 5.48 (s, 2H); 7.32 (s, 1H); 7.73 (t, 1H); 7.87 (d, 1H); 7.93 (d, 1H); 8.11 (s, 1H); 8.24 (t, 1H); 8.42 (s, 1H); 8.63 (s, 1H) ppm.

Example 1.3

[6-Bromo-7-(3-methanesulphonylbenzyloxy)quinazolin-4-yl](2-methoxyethyl)-amine

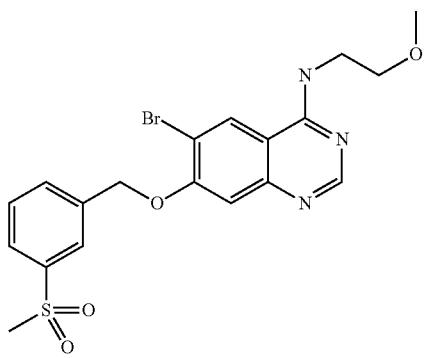 [SMILES: COCCNc1ncnc2cc(OCc3cccc(S(C)(=O)=O)c3)c(Br)cc12]

In the same way as for Example 1.1, compound 1.1.a.4 was reacted with 2-methoxy-ethylamine (yield 84%, colourless crystals).

¹H-NMR (400 MHz, DMSO-d6): δ 3.25 (s, 3H); 3.28 (s, 3H); 3.55 (t, 2H); 3.67 (q, 2H); 5.48 (s, 2H); 7.33 (s, 1H); 7.73 (t, 1H); 7.87 (d, 1H); 7.93 (d, 1H); 8.11 (s, 1H); 8.35 (t, 1H); 8.43 (s, 1H); 8.67 (s, 1H) ppm.

Example 1.4

2-[6-Bromo-7-(3-methanesulphonylbenzyloxy)quinazolin-4-ylamino]ethanol

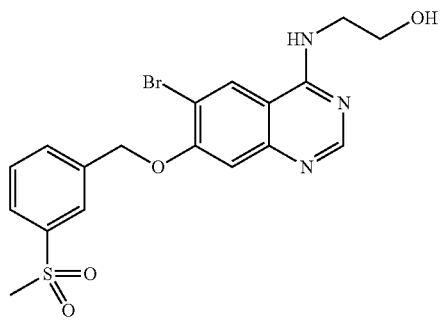 [SMILES: CS(=O)(=O)c1cccc(COc2cc3ncnc(NCCO)c3cc2Br)c1]

In the same way as for Example 1.1, compound 1.1.a.4 was reacted with ethanolamine (yield 52%, colourless crystals).

¹H-NMR (400 MHz, DMSO-d6): δ 3.95 (s, 3H); 3.56-3.64 (m, 4H); 4.87 (br, 1H); 5.48 (s, 2H); 7.33 (s, 1H); 7.73 (t, 1H); 7.87 (d, 1H); 7.93 (d, 1H) 8.11 (s, 1H); 8.32 (t, 1H); 8.41 (s, 1H); 8.66 (s, 1H) ppm.

Example 1.5

[6-Bromo-7-(3-methanesulphonylbenzyloxy) quinazolin-4-yl](1H-pyrazol-3-yl)-amine

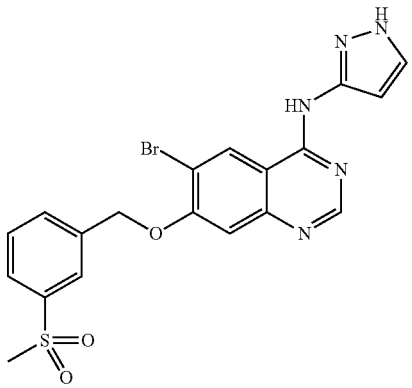 [SMILES: CS(=O)(=O)c1cccc(COc2cc3ncnc(Nc4cc[nH]n4)c3cc2Br)c1]

In the same way as for Example 1.1, compound 1.1.a.4 is reacted with 1 H-pyrazol-3-amine (yield 74%, colourless crystals).

¹H-NMR (400 MHz, DMSO-d6): δ 3.25 (s, 3H); 5.52 (s, 2H); 6.81 (s, 1H); 7.41 (s, 1H); 7.69 (s, 1H); 7.74 (s, 1H); 7.90 (d, 1H); 7.94 (m, 1H); 8.12 (s, 1H); 8.56 (s, 1H); 9.07 (s, 1H); 10.46 (br, 1H); 12.50 (br, 1H) ppm.

Example 1.6

[6-Bromo-7-(3-methanesulphonylbenzyloxy) quinazolin-4-yl][1,3,4]thiadiazol-2-ylamine

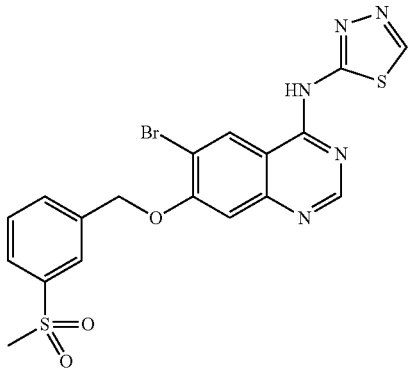 [SMILES: CS(=O)(=O)c1cccc(COc2cc3ncnc(Nc4nncs4)c3cc2Br)c1]

In the same way as for Example 1.1, compound 1.1.a.4 was reacted with 1,3,4-thiadiazol-2-amine (yield 32%, cream-coloured crystals).

¹H-NMR (400 MHz, DMSO-d6): δ 3.25 (s, 3H); 5.44 (s, 2H); 7.51 (s, 1H); 7.75 (t, 1H); 7.90 (m, 1H); 7.95 (m, 1H); 8.13 (t, 1H); 8.80 (s, 1H); 9.10 (br, 1H); 9.19 (s, 1H); 12.90 (br, 1H) ppm.

Example 1.7

[6-Bromo-7-(3-methanesulphonylbenzyloxy) quinazolin-4-yl]cyclopropylamine

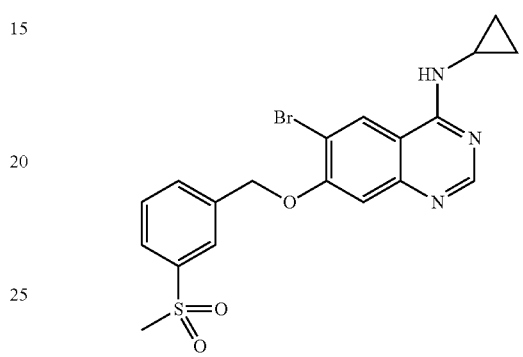

In the same way as for Example 1.1, compound 1.1.a.4 was reacted with cyclopropylamine (yield 61%, colourless crystals).

¹H-NMR (400 MHz, DMSO-d6): δ 0.60-0.66 (m, 2H); 0.76-0.82 (m, 2H); 2.97-3.06 (m, 1H); 3.24 (s, 3H); 5.48 (s, 2H); 7.34 (s, 1H); 7.73 (t, 1H); 7.87 (dt, 1H); 7.94 (dt, 1H); 8.11 (t, 1H); 8.22 (d, 1H); 8.48 (s, 1H); 8.61 (s, 1H) ppm.

Example 1.8

[6-Bromo 7-(3-methanesulphonylbenzyloxy) quinazolin-4-yl]cyclobutylamine

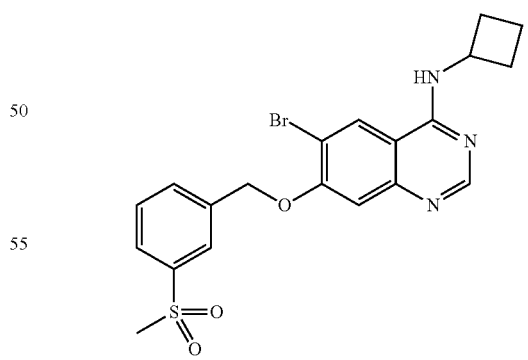

In the same way as for Example 1.1, compound 1.1.a.4 was reacted with cyclobutylamine (yield 78%, colourless crystals).

¹H-NMR (400 MHz, DMSO-d6): δ 1.69-1.78 (m, 2H); 2.04-2.17 (m, 2H); 2.27-2.37 (m, 2H); 3.24 (s, 3H); 4.61-4.74

(m, 1H); 5.48 (s, 2H); 7.32 (s, 1H); 7.73 (t, 1H); 7.88 (dt, 1H); 7.94 (dt, 1H); 8.11 (t, 1H); 8.32 (d, 1H); 8.41 (s, 1H); 8.71 (s, 1H) ppm.

Example 1.9

[6-Bromo-7-(3-methanesulphonylbenzyloxy)quinazolin-4-yl]cyclopropylmethyl-amine

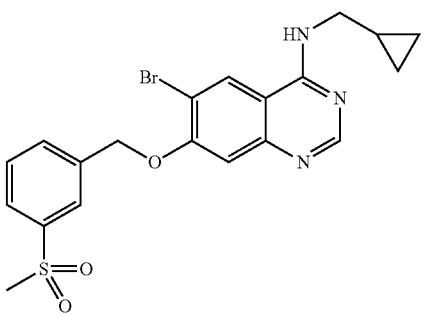 [SMILES: CS(=O)(=O)c1cccc(COc2cc3ncnc(NCC4CC4)c3cc2Br)c1]

In the same way as for Example 1.1, compound 1.1.a.4 was reacted with cyclopropylmethylamine (yield 69%, colourless crystals).

$^1$H-NMR (400 MHz, DMSO-d6): δ 0.25-0.30 (m, 2H); 0.44-0.50 (m, 2H); 1.11-1.21 (m, 1H); 3.25 (s, 3H); 3.31-3.39 (m, 2H); 5.48 (s, 2H); 7.33 (s, 1H); 7.73 (t, 1H); 7.88 (dt, 1H); 7.94 (dt, 1H); 8.11 (t, 1H); 8.36 (t, 1H); 8.41 (s, 1H); 8.68 (s, 1H) ppm.

Example 1.10

N'-[6-Bromo-7-(3-methanesulphonylbenzyloxy)quinazolin-4-yl]-N,N-dimethylethane-1,2-diamine

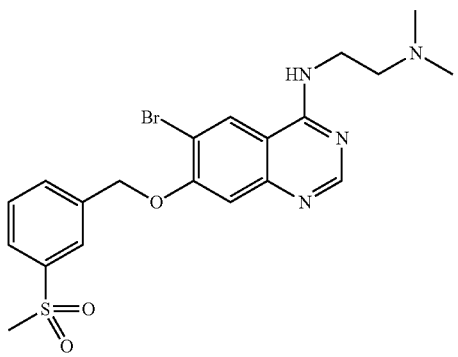 [SMILES: CN(C)CCNc1ncnc2cc(OCc3cccc(S(C)(=O)=O)c3)c(Br)cc12]

In the same way as for Example 1.1, compound 1.1.a.4 was reacted with N,N-dimethylethylenediamine (yield 47%, colourless crystals).

$^1$H-NMR (400 MHz, DMSO-d6): δ 2.20 (s, 6H); 3.24 (s, 3H); 3.64 (q, 4H); 5.48 (s, 2H); 7.33 (s, 1H); 7.73 (t, 1H); 7.88 (d, 1H); 7.93 (dt, 1H); 8.11 (1H); 8.21 (t, 1H); 8.42 (s, 1H); 8.63 (s, 1H) ppm.

Example 1.11

Cyclopropyl[7-(3-methanesulphonylbenzyloxy)-6-methoxyquinazolin-4-yl]amine

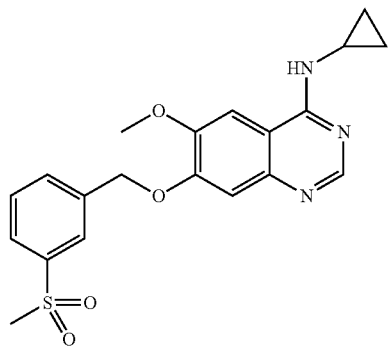 [SMILES: COc1cc2c(NC3CC3)ncnc2cc1OCc1cccc(S(C)(=O)=O)c1]

1.11a) Preparation of the Intermediates

Compound 1.11.a)

(E/Z)-N'-[2-Cyano-5-(3-methanesulphonylbenzyloxy)-4-methoxyphenyl]-N,N-dimethylformamidine

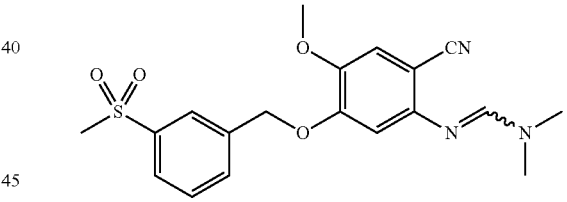

Preparation took place in the same way as for compound 1.1.a.4.

$^1$H-NMR (400 MHz, DMSO-d6): δ 2.96 (s, 3H); 3.06 (s, 3H); 3.25 (s, 3H); 3.74 (s, 3H); 5.28 (s, 3H); 6.90 (s, 1H); 7.14 (s, 1H); 7.71 (t, 1H); 7.80 (d, 1H); 7.88 (s, 1H); 7.92 (d, 1H); 8.05 (s, 1H) ppm.

1.11b) Preparation of the Final Product 120 mg of the intermediate prepared under 1.11.a) were dissolved in 0.65 ml of acetonitrile. Following addition of 85 μl of glacial acetic acid and 25 μl of cyclopropylamine, the solution was heated in the microwave at 160° C. for 60 minutes. The reaction solution was evaporated. The residue obtained was purified by chromatography. This gave 53 mg of cyclopropyl[7-(3-methanesulphonylbenzyloxy)-6-methoxyquinazolin-4-yl]amine as a colourless foam.

$^1$H-NMR (400 MHz, DMSO-d6): δ 0.59-0.64 (m, 2H); 0.78-0.84 (m, 2H); 2.92-3.01 (m, 1H); 3.24 (s, 3H); 3.90 (s,

3H); 5.37 (s, 2H); 7.23 (s, 1H); 7.60 (1H); 7.71 (s, 1H); 7.84 (d, 1H); 7.91-7.97 (m, 2H); 8.07 (1H); 8.39 (s, 1H) ppm.

Example 1.12

Cyclobutyl[7-(3-methanesulphonylbenzyloxy)-6-methoxyquinazolin-4-yl]amine

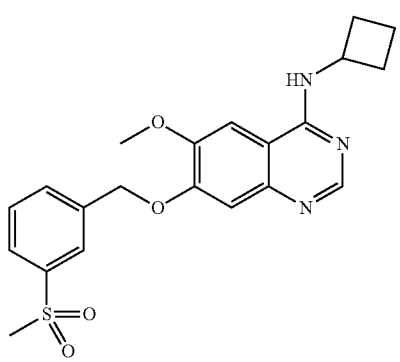 [SMILES: COc1cc2c(NC3CCC3)ncnc2cc1OCc1cccc(S(C)(=O)=O)c1]

In the same way as, for Example 1.7, compound 1.11.a was reacted with cyclobutylamine (yield 46%, colourless foam).

$^1$H-NMR (400 MHz, DMSO-d6): δ 1.70-1.79 (m, 2H); 2.05-2.18 (m, 2H); 2.30-2.39 (m, 2H); 3.25 (s, 3H); 3.92 (s, 3H); 4.64-4.77 (m, 1H); 5.37 (s, 2H); 7.21 (s, 1H); 7.67 (s, 1H); 7.71 (t, 1H); 7.85 (dt, 1H); 7.93 (dt, 1H); 7.99 (d, 1H); 8.07 (t, 1H); 8.14 (s, 1H) 8.32 (s, 1H) ppm.

Example 1.13

[7-(3-Methanesulphonylbenzyloxy)-6-methoxyquinazolin-4-yl]pyridin-4-ylamine

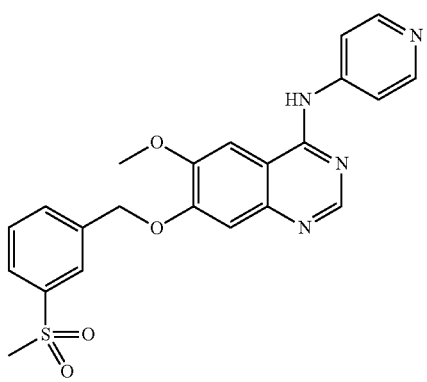 [SMILES: COc1cc2c(Nc3ccncc3)ncnc2cc1OCc1cccc(S(C)(=O)=O)c1]

In the same way as for Example 1.7, compound 1.11.a was reacted with 4-aminopyridine (yield 33%, colourless foam).

$^1$H-NMR (400 MHz, DMSO-d6): δ 3.26 (s, 3H); 4.01 (s, 3H); 5.44 (s, 2H); 7.41 (s, 1H); 7.73 (t, 1H); 7.86-7.96 (m, 5H); 8.10 (1H); 8.49 (d, 2H); 8.63 (s, 1H); 9.75 (sbr, 1H) ppm.

Example 1.14

[7-(3-Methanesulphonylbenzyloxy)-6-methoxyquinazolin-4-yl]pyridin-3-ylamine

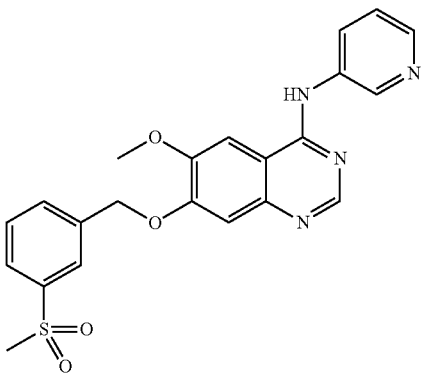 [SMILES: COc1cc2c(Nc3cccnc3)ncnc2cc1OCc1cccc(S(C)(=O)=O)c1]

In the same way as for Example 1.7, compound 1.11.a was reacted with 3-aminopyridine (yield 21%, colourless foam).

$^1$H-NMR (400 MHz, DMSO-d6): δ 3.26 (s, 3H); 3.99 (s, 3H); 5.43 (s, 2H); 7.36 (s, 1H); 7.44 (dd, 1H); 7.73 (t, 1H); 7.88 (dt, 1H); 7.90 (s, 1H); 7.94 (dt, 1H); 8.09 (1H); 8.23-8.27 (m, 1H); 8.32 (dd, 1H); 8.49 (s, 1H); 8.95 (d, 1H); 9.67 (s, 1H) ppm.

Example 1.15

5-[7-(3-Methanesulphonylbenzyloxy)-6-methoxyquinazolin-4-ylamino]pyridin-2-ol

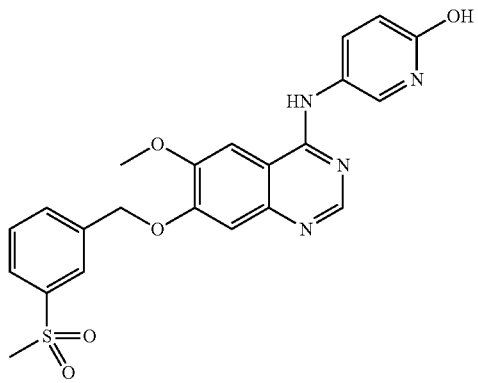 [SMILES: COc1cc2c(Nc3ccc(O)nc3)ncnc2cc1OCc1cccc(S(C)(=O)=O)c1]

In the same way as for Example 1.7, compound 1.11.a was reacted with 5-aminopyridin-2-ol (yield 39%, grey solid).

1H-NMR (400. MHz, DMSO-d6): δ 3.27 (s, 3H); 4.01 (s, 3H); 5.46 (s, 2H); 6.45 (d, 1H); 7.42 (s, 1H); 7.72-7.78 (m, 3H); 7.88 (d, 1H); 7.96 (dt, 1H); 8.10 (1H); 8.29 (s, 1H); 8.80 (s, 1H); 11.26 (s, 1H) ppm.

Example 1.16

[7-(3-Methanesulphonylbenzyloxy)-6-methoxyquinazolin-4-yl]thiazol-2-ylamine

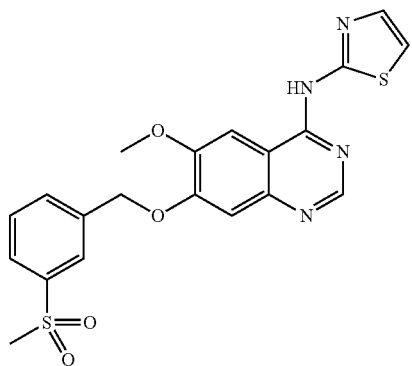 [SMILES: COc1cc2c(Nc3nccs3)ncnc2cc1OCc1cccc(S(C)(=O)=O)c1]

In the same way as for Example 1.7, compound 1.11.a was reacted with thiazol-2-ylamine (yield 36%, colourless foam).

1H-NMR (400 MHz, DMSO-d6): δ 3.26 (s, 3H); 3.98 (s, 3H); 5.44 (s, 2H); 7.27 (d, 1H); 7.41 (s, 1H); 7.56 (d, 1H); 7.73 (t, 1H); 7.87 (d, 1H); 7.94 (dt, 1H); 8.09 (1H); 8.18 (s, 1H); 8.69 (s, 1H); 12.18 (br, 1H) ppm.

Process Variant 2

Example 2.1

Isopropyl[7-(3-methanesulphonylbenzyloxy)-6-methoxyquinazolin-4-yl]amine

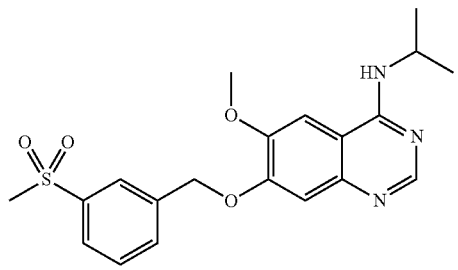 [SMILES: COc1cc2c(NC(C)C)ncnc2cc1OCc1cccc(S(C)(=O)=O)c1]

2.1a) Preparation of the Intermediate 4-(Isopropylamino)-6-methoxyquinazolin-7-ol

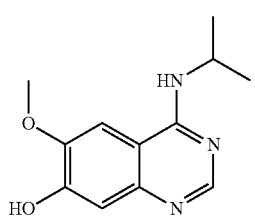 [SMILES: COc1cc2c(NC(C)C)ncnc2cc1O]

The (E/Z)-N'-(2-cyano-5-hydroxy-4-methoxyphenyl)-N,N-dimethyl-formimidamide (0.62 g, 2.25 mmol) prepared according to WO2004/58752 is reacted with isopropylamine (0.16 g, 2.7 mmol) in acetonitrile (3 ml) and acetic acid (0.7 ml) and radiated with microwaves with stirring for 10 minutes at 160° C. (cf. Y. Hang, Org. Lett., 2004, 6, 4775-4778). After cooling to room temperature, the batch is rendered alkaline by means of saturated sodium hydrogencarbonate solution and extracted with ethyl acetate. Concentrating the organic phase, the desired product is obtained in 55% yield (310 mg).

1H-NMR (400 MHz, DMSO-d6): δ 1.26 (d, 6H), 3.91 (s, 3H), 4.49 (dsept, 1H), 6.94 (s, 1H), 7.45 (d, 1H), 7.59 (s, 1H), 8.25 (s, 1H), 10.08 (br s, 1H).

2.1b) Preparation of the Final Product 4-(Isopropylamino)-6-methoxyquinazolin-7-ol (30 mg, 0.13 mmol) is initially charged in 5 mL of acetone, admixed with 3-methylsulphonylbenzyl bromide (40 mg, 0.16 mmol) prepared as described in US 2005/222175 and US2004-94-7995 and also potassium carbonate (28 mg, 0.2 mmol) and subsequently refluxed for 6 hours. After cooling to room temperature, the batch is diluted with ethyl acetate. The organic phase is washed with water and dried over sodium sulphate. Following concentrating of the solvent and also preparative thin layer chromatography (silica gel, dichloromethane/methanol: 9/1) the desired compound is obtained in 40% yield (21 mg).

1H-NMR (300 MHz, DMSO-d6): δ 1.28 (d, 6H), 3.25 s, 3H), 3.93 (s, 3H), 4.47-4.54 (m, 1H), 5.38 (d, 2H), 7.21 (s, 1H), 7.57 (d, 1H), 7.67 (s, 1H), 7.72 (t, 1H), 7.85 (d, 1H), 7.93 (d 1H), 8.08 (s, 1H), 8.33 (s, 1H).

II. Biological Actions of the Compounds According to the Invention

TLR-Induced Cytokine Release in Human "Peripheral Blood Mononuclear Cells" (PBMC)

Test Principle

PBMCs isolated from human whole blood are stimulated using a TLR ligand.

The cytokine determination is carried out by means of ELISA kits; a proliferation/cell metabolism determination is carried out using Alamar Blue.

PBMC Isolation:

For the cell preparation, about 200 ml of blood are treated with an anticoagulant (e.g. citrate Monovettes). Per Leucosep tube, 15 ml of Histopaque (room temperature, RT) are poured in and pressed downwards through the frit employed by brief initial centrifugation (one minute at 1000×g, RT). 20 ml of blood are added to the tubes prepared in this way and centrifuged at 800×g for 15 minutes (RT). After centrifugation, the following layered arrangement results from the top to the bottom: plasma—PBMC Histopaque—filter disc—Histopaque—erythrocytes and granulocytes. The supernatant plasma is aspirated. The PBMC are transferred together with the underlying Histopaque to a new 50 ml tube, the contents of two Leucosep tubes always being added to one 50 ml tube. The 50 ml tubes are then filled to 50 ml with PBS. This cell suspension is centrifuged at 300×g (RT) for 10 minutes. The liquid supernatant is tipped off and the cell pellet is resuspended with a little PBS and subsequently filled to 50 ml with PBS. This washing step is repeated twice. The resulting pellet is taken up in a defined volume of medium (with additives). For the testing of the substances, PBMC are incubated for 18 hours with titrated concentrations of the test substances, e.g. in the presence or absence of TLR ligands. On the next day, the supernatants are investigated for the content of IL-12, TNF-alpha or other chemokines by means of specific ELISA. The metabolic activity of the treated cells is determined with the aid of Alamar Blue.

Results:

| Example | IC$_{50}$ (TNF-α) |
|---------|-------------------|
| 2.1     | 3 μM              |

The invention claimed is:

1. A compound of formula (I)

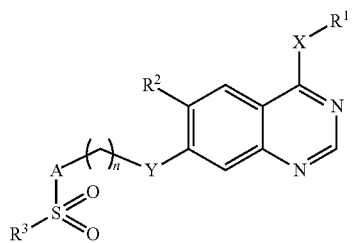

(I)

in which

R$^1$ represents a C$_1$-C$_6$-alkyl radical optionally identically or differently mono- or polysubstituted by hydroxyl, —NR$^6$R$^7$, C$_1$-C$_6$-alkoxy and/or C$_3$-C$_6$-cycloalkyl, R$^2$ represents hydrogen, halogen, cyano or a C$_1$-C$_6$-alkoxy radical, R$^3$ represents a C$_1$-C$_6$-alkyl radical X represents —NH—, Y represents —O— or —NH—, A represents a phenyl or monocyclic heteroaryl ring, n represents 1 or 2, and R$^6$ and R$^7$ independently of one another represent hydrogen or a C$_1$-C$_3$-alkyl radical, and their salts, diastereomers and enantiomers.

2. A compound according to claim 1, in which

R$^1$ represents a C$_1$-C$_3$-alkyl radical,

R$^2$ represents halogen or a C$_1$-C$_6$-alkoxy radical,

R$^3$ represents a C$_1$-C$_3$-alkyl radical,

X represents —NH—,

Y represents —O—,

A represents a phenyl ring, and n represents 1, and their salts, diastereomers and enantiomers.

3. Process for the preparation of a compound according to claim 1, comprising reacting an intermediate according to formula (II) with a compound R$^1$—XH,

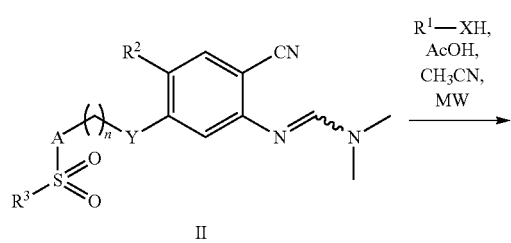

II

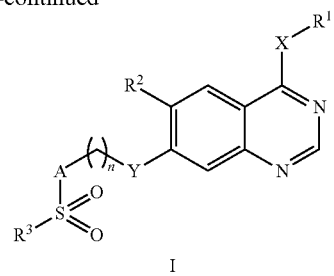

I where R$^1$, R$^2$, R$^3$ and X, Y, A and n have the meanings indicated in claim 1.

4. Process for the preparation of a compound according to claim 1, comprising reacting a quinazoline of the formula (VII) with an intermediate of the formula (IV),

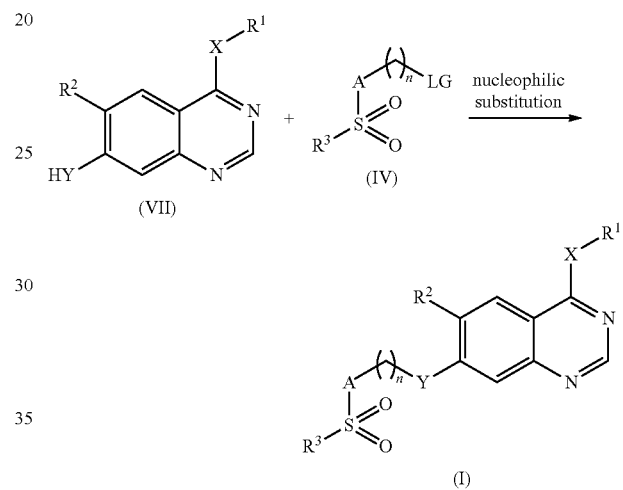

where R$^1$, R$^2$, R$^3$ and X, Y, A and n have the meanings indicated in claim 1.

5. Process for the preparation of a compound according to claim 1, comprising oxidizing an intermediate of the formula (VII) to the corresponding sulphone

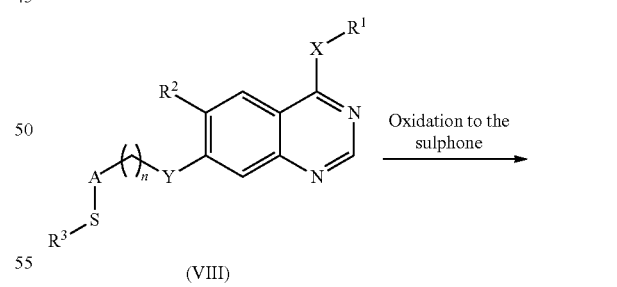

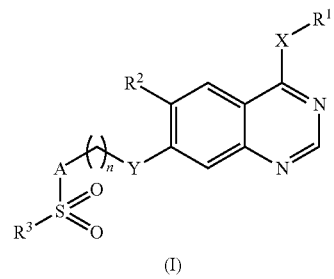

(I)

where $R^1$, $R^2$, $R^3$ and X, Y, A and n have the meanings indicated in claim 1.
6. An intermediate of the formula (II):
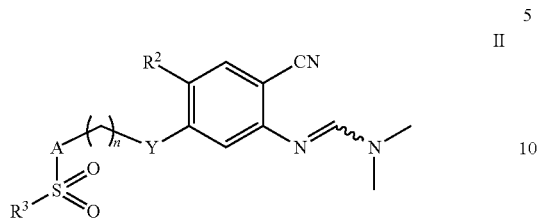
where $R^2$, $R^3$ and Y, A and n have the meanings indicated in claim 1.
7. A pharmaceutical formulation comprising a compound according to claim 1 and a pharmaceutically acceptable excipient.
* * * * *